United States Patent
Arth et al.

(10) Patent No.: US 7,807,715 B2
(45) Date of Patent: Oct. 5, 2010

(54) PHARMACEUTICAL COMPOSITIONS COMPRISING FESOTERODINE

(75) Inventors: Christoph Arth, Düsseldorf (DE); Michael Komenda, Köln (DE); Fatima Bicane, Rösrath (DE); Hans-Jurgen Mika, Bonn (DE)

(73) Assignee: UCB Pharma GmbH, Monheim (DE)

( * ) Notice: Subject to any disclaimer, the term of this patent is extended or adjusted under 35 U.S.C. 154(b) by 0 days.

(21) Appl. No.: 11/811,327

(22) Filed: Jun. 7, 2007

(65) Prior Publication Data

US 2008/0138421 A1    Jun. 12, 2008

Related U.S. Application Data

(60) Provisional application No. 60/812,149, filed on Jun. 9, 2006.

(51) Int. Cl.
*A01N 37/02* (2006.01)
*A61K 31/22* (2006.01)
*A61K 9/14* (2006.01)

(52) U.S. Cl. ...................................... 514/546; 424/489
(58) Field of Classification Search ....................... None
See application file for complete search history.

(56) References Cited

U.S. PATENT DOCUMENTS 5,204,115 A * 4/1993 Olinger et al. .............. 424/470
2005/0031685 A1 * 2/2005 Sen et al. .................... 424/468
2005/0191352 A1 * 9/2005 Hayes et al. ................ 424/468
2006/0018957 A1 * 1/2006 Lerner et al. ................ 424/451
2008/0318982 A1 * 12/2008 Mastrell et al. .......... 514/262.1

FOREIGN PATENT DOCUMENTS

| WO | 99/58478 | 11/1999 |
| WO | 01/35957 | 5/2001 |

* cited by examiner

*Primary Examiner*—Frederick Krass
*Assistant Examiner*—Marcos Sznaidman
(74) *Attorney, Agent, or Firm*—Kenyon & Kenyon LLP

(57) ABSTRACT

The present application relates to a pharmaceutical granulate comprising Fesoterodine or a pharmaceutically acceptable salt or solvate thereof and a pharmaceutically acceptable stabilizer, which can be selected from the group consisting of sorbitol, xylitol, polydextrose, isomalt, dextrose, and combinations thereof, and is preferably a sugar alcohol selected from the group consisting of xylitol and sorbitol. The granulate is suitable for incorporation into pharmaceutical compositions comprising a gel matrix formed by at least one type of hydroxypropyl methylcellulose into which the Fesoterodine is embedded and, optionally, further excipients. In certain embodiments, the granulate is formed by a process of wet granulation.

9 Claims, 9 Drawing Sheets

PHARMACEUTICAL COMPOSITIONS COMPRISING FESOTERODINE

PRIORITY CLAIM

This application claims benefit and priority under 35 U.S.C. §119(e) of U.S. Provisional Patent Application Ser. No. 60/812,149 filed on Jun. 9, 2006, the entirety of which is expressly incorporated herein by reference thereto.

FIELD OF THE INVENTION

The present invention generally relates to a pharmaceutical composition comprising Fesoterodine or a pharmaceutically acceptable salt or solvate thereof and to a method for its preparation.

BACKGROUND

Fesoterodine of formula (I) can be chemically described as 2-[(1R)-3-(diisopropylamino)-1-phenylpropyl]-4-(hydroxymethyl)phenyl isobutyrate.

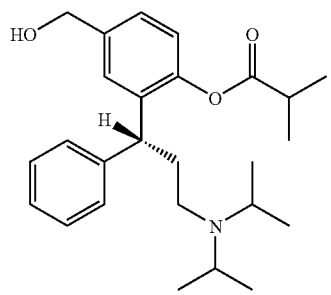

(I)

Fesoterodine is an innovative drug for the treatment of overactive bladder, urinary incontinence and other dysfunctions of the urinary tract. It is disclosed, inter alia, in EP 1077912 B1, pertaining to novel derivatives of 3,3-diphenylpropylamines. EP 1230209 B1 discloses stable salts of novel derivatives of 3,3-diphenylpropylamines, including Fesoterodine hydrogen fumarate.

Overactive bladder (OAB) is an extremely common disorder, affecting 17% of the adult population in major European countries. OAB can occur at any age and in either gender, although its prevalence is higher in geriatric and female populations.

OAB is a bladder function disorder resulting in symptoms of urgency, with or without urge incontinence, and usually includes increased urinary frequency and nocturia. The disorder is due to spastic contractions of the detrusor muscle of the bladder, resulting in sustained high bladder pressure and the urgent need to urinate. This can be caused by several reasons, such as traumatic or toxic nerve damage (e.g., abdominal trauma, pelvic trauma or surgery, bladder stones, adverse effects of drugs), neurological diseases (e.g., spinal cord lesions, multiple sclerosis, Parkinson's disease, excessive neurotransmitter release in the bladder) or myogenic instability (e.g., bladder hypertrophy caused by outlet obstruction or urinary tract infection).

In some cases, OAB can be managed without pharmacotherapy, using exercise, pessaries, implants, biofeedback or behavioral therapy. But in most cases, pharmacotherapy is the better option. Antimuscarinic agents have been found to be particularly effective for treating OAB. During normal micturition, acetylcholine released from postganglionic parasympathetic neurons acts on the muscarinic receptors of the detrusor smooth muscle in the bladder to stimulate contractions. Antimuscarinic agents interfere with this action, thus reducing detrusor contractions. However, despite the availability of different antimuscarinic drugs, physicians and patients remain dissatisfied with current treatments due to adverse events and/or insufficient efficacy. Furthermore, as a general matter, it is desirable for pharmaceutical compounds to have as little effect on QT intervals as possible. In particular, it is desirable that there be no significant QT/QTc interval prolongation. Therefore, new agents with improved safety and efficacy are needed for a more effective treatment of OAB.

Fesoterodine is known in the art for its potency in treating urinary incontinence. However, Fesoterodine may exhibit substantial degradation under stress conditions, e.g., in a humid environment and at increased temperature. It is believed that hydrolyzation and oxidation are among the major mechanisms resulting in degradation. Therefore, it would be desirable to develop new pharmaceutical compositions comprising Fesoterodine that are more stable against degradation over an extended period of time even under stress conditions. To that end, it has now been found, surprisingly, that some pharmaceutical excipients are able to significantly slow down the degradation of Fesoterodine under stress conditions.

SUMMARY OF THE INVENTION

In one aspect, disclosed is a pharmaceutical composition comprising Fesoterodine or a pharmaceutically acceptable salt or solvate thereof and a stabilizer.

In another aspect, disclosed is a pharmaceutical composition for the oral administration of Fesoterodine, the composition comprising Fesoterodine or a pharmaceutically acceptable salt or solvate thereof and a stabilizer.

In another aspect, disclosed is a granulate of Fesoterodine and a stabilizer, preferably a pharmaceutically acceptable stabilizer. In another aspect, disclosed is a pharmaceutical composition comprising a granulate of Fesoterodine and a stabilizer, preferably a pharmaceutically acceptable stabilizer.

Also disclosed is a pharmaceutical composition, preferably a solid pharmaceutical composition, comprising Fesoterodine or a pharmaceutically acceptable salt or solvate thereof and a stabilizer selected from the group consisting of sorbitol, xylitol, polydextrose, isomalt, dextrose, and combinations thereof and at least one further excipient, preferably at least one type of hydroxypropyl methylcellulose.

In another aspect, disclosed is a granulate comprising Fesoterodine or its pharmaceutically acceptable salt or solvate and a stabilizer selected from the group consisting of sorbitol, xylitol, polydextrose, isomalt, dextrose, and combinations thereof. In another aspect, disclosed is a pharmaceutical composition comprising a granulate of Fesoterodine or its pharmaceutically acceptable salt or solvate and a stabilizer selected from the group consisting of sorbitol, xylitol, polydextrose, isomalt, dextrose, and combinations thereof.

In yet another aspect, presently disclosed is a pharmaceutical composition for the oral administration of Fesoterodine or a pharmaceutically acceptable salt or solvate thereof that may be obtained by granulating Fesoterodine with a suitable excipient, preferably a stabilizer selected from the group consisting of sorbitol, xylitol, polydextrose, isomalt, dextrose, and combinations thereof. Preferably, the stabilizer is a sugar alcohol chosen from among xylitol and sorbitol, and more preferably xylitol. The granulate then may be combined or mixed with at least one further excipient, preferably at least one type of hydroxypropyl methylcellulose, and optionally other excipients.

In another aspect, disclosed is a pharmaceutical composition comprising Fesoterodine or a pharmaceutically acceptable salt or solvate thereof, wherein the pharmaceutical composition can be solid, and may be suitable for oral administration. Fesoterodine, or a salt thereof, further can be embedded in a gel matrix formed by at least one type of hydroxypropyl methylcellulose (hypromellose) and, optionally, further excipients. More preferably, Fesoterodine and a stabilizer may be embedded in a gel matrix formed by at least one type of hydroxypropyl methylcellulose (hypromellose) and, optionally, further excipients.

In certain embodiments, the fesoterodine salt can be a salt of a polybasic acid, preferably with an auto pH in water in the range of about 3-5 (measured in water at 25° C. at a concentration of 1 wt %). Examples may be chosen from the group of polybasic mineral acids, such as e.g. sulfuric acid and phosphoric acid, or of polybasic organic acids. Preferred examples are salts of di- or tricarboxylic acids such as fesoterodine maleate, fesoterodine oxalate, fesoterodine citrate, fesoterodine phthalate, fesoterodine fumarate, fesoterodine succinate, fesoterodine tartrate, fesoterodine malonate, fesoterodine malate, etc. In particular embodiments, the fesoterodine salt may be a partially hydrogenated di- or tricarboxylic acid salt, particularly a salt with an auto pH of 3-5, particularly between 3 and 4, more preferably between 3.25 and 3.75, such as hydrogen fumarate or hydrogen maleate. A particularly preferred salt is fesoterodine hydrogen fumarate.

In yet another aspect, disclosed is a pharmaceutical composition as described above comprising Fesoterodine fumarate as a pharmaceutically acceptable salt, and preferably, Fesoterodine hydrogen fumarate.

In another aspect, disclosed is a pharmaceutical composition as described above comprising Fesoterodine or a pharmaceutically acceptable salt, preferably Fesoterodine hydrogen fumarate, or the free base, in an amount of about 0.5-28 mg, or about 0.5-20 mg, preferably about 1-16 mg, about 1-12 mg, more preferably about 1-8 mg, and even more preferably about 2, about 4 or about 8 mg per dosage unit (based on the content of Fesoterodine or its salt, e.g., Fesoterodine hydrogen fumarate), or free base.

Also disclosed is a method of treating patients suffering from overactive bladder and having symptoms such as urinary incontinence, specifically urinary urge incontinence, urinary urgency and/or urinary frequency by administering a therapeutically effective amount of any of the compositions as described herein. In particular, disclosed is a method of treating patients suffering from overactive bladder that may have symptoms such as urinary incontinence, urinary urge incontinence, urinary urgency and/or urinary frequency by administering a unit dosage form of the Fesoterodine compositions described herein. A unit dosage form may contain between about 0.5-28 mg or about 0.5-20 mg Fesoterodine, preferably about 1-16 mg or about 1-12 mg, more preferably about 1-8 mg, and even more preferably about 2, about 4 or about 8 mg per dosage unit (based on the content of Fesoterodine or its salt, e.g., Fesoterodine hydrogen fumarate), or the free base. The unit dosage form can be administered once-daily to a patient or, in some cases, more than once daily to a patient, as may be appropriate.

Moreover, presently disclosed is a method for the production of a pharmaceutical composition as described above comprising producing a mixture containing Fesoterodine or a pharmaceutically acceptable salt thereof and a stabilizer selected from the group consisting of sorbitol, xylitol, polydextrose, isomalt, dextrose, and combinations thereof. Preferably, the stabilizer is a sugar alcohol chosen from among xylitol and sorbitol, and preferably xylitol. These components then can be mixed or combined with at least one type of hydroxypropyl methylcellulose, and optionally other excipients. Optionally, the resultant composition may be pressed into tablets and coated.

One preferred method for the production of a pharmaceutical composition containing Fesoterodine comprises granulating Fesoterodine or a pharmaceutically acceptable salt thereof and a stabilizer selected from the group consisting of sorbitol, xylitol, polydextrose, isomalt, dextrose, and combinations thereof, preferably a sugar alcohol chosen from among xylitol and sorbitol, and more preferably xylitol, and then mixing or combining the granulate thus formed with at least one type of hydroxypropyl methylcellulose, and optionally other excipients. The resultant composition then may be pressed into tablets and coated.

The granulation process may be performed in a dry granulation procedure, without the addition of liquid or, preferably, in the presence of a liquid, such as water ("wet granulation"). In wet granulation, for example, Fesoterodine or a pharmaceutically acceptable salt thereof and a stabilizer selected from the group consisting of sorbitol, xylitol, polydextrose, isomalt, dextrose, and combinations thereof, preferably a suitable sugar alcohol, preferably sorbitol or xylitol, and more preferably xylitol, can be mixed or combined in the presence of water. The granulate then can be dried. This dried granulate then may be mixed or combined with at least one further excipient, preferably at least one type of hydroxypropyl methylcellulose, and optionally other excipients.

It has been surprisingly found that wet granulation can be accomplished without increasing the degradation of Fesoterodine due to hydrolyzation of the ester bond. For the same reason, it was even more surprising that Fesoterodine is more stable in a composition that is produced in the presence of water, e.g., by wet granulation, than in a composition that is produced by dry granulation (see, e.g., Table 9) or by dry mixing and compressing the excipients (see, e.g., Table 8).

In another and more general aspect, the present invention relates to a pharmaceutical composition comprising fesoterodine, or a pharmaceutically acceptable salt or solvate thereof, and a pharmaceutically acceptable stabilizer, wherein the stabilizer is identified by a method comprising the following steps:

preparing a binary granulate of 1 part by weight of fesoterodine and 9 parts by weight of the stabilizer; storing said granulate under the following three conditions:
a) 25° C. and 60% r.H. in. closed vials for 6 weeks
b) 40° C. and 75% r.H. in closed vials for 6 weeks
c) 40° C. and 75% r.H. in open vials for 6 weeks
determining the content of the Active Metabolite of Formula II

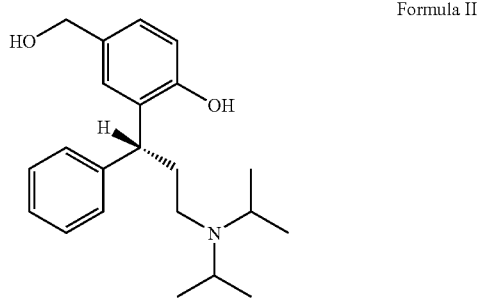

Formula II via HPLC by the area-% method;
selecting a stabilizer from those which limit the formation of Active Metabolite of Formula II during storage under at least two of the above conditions as follows:
i) about 1 wt % or less under storage condition a)

ii) about 2 wt % or less under storage condition b)

iii) about 2 wt % or less under storage condition c)

Preferably, such stabilizer is selected from polyols, sugars or sugar alcohols. Most preferably this stabilizer is xylitol, sorbitol, polydextrose, isomalt, dextrose or combinations thereof, and even more preferably xylitol, sorbitol or polydextrose. The composition containing the stabilizer preferably comprises a salt of Fesoterodine which has an auto pH in water of 3-5. Auto pH is the pH value which can be measured after dissolving 1 wt-% Fesoterodine salt in water at 25° C.

The pharmaceutical compositions comprising Fesoterodine and a stabilizer disclosed herein do not significantly increase QT intervals, e.g., QTcF or QTcI. Therefore, also disclosed are pharmaceutical compositions comprising Fesoterodine and a stabilizer, preferably a sugar alcohol such as xylitol or sorbitol, which pharmaceutical compositions do not significantly increase QT intervals such as QTcF or QTcI. Such pharmaceutical compositions may exhibit a mean time average QTcF or QTcI decrease of about 4.6 ms to about 5.0 ms after three days of treatment. The pharmaceutical compositions having such QTcF or QTcI characteristics may contain between about 4 mg and about 28 mg of Fesoterodine. Preferably, the pharmaceutical compositions are solid compositions such as tablets containing about 4 mg, about 5 mg, about 6 mg, about 7 mg, about 8 mg, about 9 mg, about 10 mg, about 12 mg, about 16 mg, about 20 mg, about 24 mg, or about 28 mg of Fesoterodine. In particular embodiments, the pharmaceutical compositions contain between about 4 mg and about 12 mg, preferably between about 4 mg and about 8 mg, of Fesoterodine and have the effect on QTcF or QTcI described above and furthermore may cause dry mouth in not more than about 22% to about 34% of patients when administered once-daily. In preferred embodiments, the pharmaceutical compositions have these effects with respect to QT intervals and dry mouth and contain about 4 mg, about 5 mg, about 6 mg, about 7 mg, about 8 mg, about 9 mg, about 10 mg, about 12 mg, about 16 mg, about 20 mg, about 24 mg, or about 28 mg of Fesoterodine.

Disclosed also is a method of treatment for overactive bladder and related conditions comprising the administration to a patient in need thereof of a pharmaceutical composition comprising Fesoterodine and a stabilizer wherein the method does not lead to a significant increase in QTcF or QTcI. In certain embodiments, the method leads to a mean time average QTcF or QTcI decrease of about 4.6 ms to about 5.0 ms after three days of treatment. In certain embodiments, between about 4 mg to about 28 mg of Fesoterodine per day is administered. Preferably, about 4 mg per day, about 5 mg per day, about 6 mg per day, about 7 mg per day, about 8 mg per day, about 9 mg per day, about 10 mg per day, about 12 mg per day, about 16 mg per day, about 20 mg per day, about 24 mg per day, or about 28 mg per day of Fesoterodine is administered.

Disclosed also is a method of treatment for overactive bladder and related conditions comprising the administration to a patient in need thereof of a pharmaceutical compositions comprising Fesoterodine and a stabilizer wherein the method does not lead to a significant increase in QTcF or QTcI, in particular wherein the method leads to a mean time average QTcF or QTcI decrease of about 4.6 ms to about 5.0 ms after three days of treatment, and wherein the method causes dry mouth in not more than about 22% of patients when about 4 mg of Fesoterodine is administered once-daily or wherein the method causes dry mouth in not more than about 34% of patients when about 8 mg of Fesoterodine is administered once-daily. Preferably, the method comprises the administration of about 4 mg to about 12 mg of Fesoterodine per day. Especially preferred is the administration of about 4 mg, about 5 mg, about 6 mg, about 7 mg, about 8 mg, about 9 mg, about 10 mg, about 11 mg, or about 12 mg of Fesoterodine per day.

Also disclosed is a pharmaceutical composition comprising Fesoterodine and a stabilizer that exhibits a low level of adverse events. Disclosed is a pharmaceutical composition comprising about 4 mg of Fesoterodine and a stabilizer selected from the group consisting of sorbitol, xylitol, polydextrose, isomalt, dextrose, and combinations thereof, preferably a sugar alcohol such as xylitol or sorbitol, which pharmaceutical composition causes dry mouth in not more than about 22% of patients when administered once-daily. Also disclosed is a pharmaceutical composition comprising about 8 mg of Fesoterodine and a stabilizer selected from the group consisting of sorbitol, xylitol, polydextrose, isomalt, dextrose, and combinations thereof, preferably a sugar alcohol such as xylitol or sorbitol, which pharmaceutical composition causes dry mouth in not more than about 34% of patients when administered once-daily. Also disclosed is a method of treating overactive bladder or related conditions comprising administering a pharmaceutical composition comprising about 4 mg of Fesoterodine and a stabilizer selected from the group consisting of sorbitol, xylitol, polydextrose, isomalt, dextrose, and combinations thereof, preferably a sugar alcohol such as xylitol or sorbitol, which pharmaceutical composition causes dry mouth in not more than about 22% of patients when administered once-daily.

Also disclosed are pharmaceutical compositions comprising Fesoterodine and a stabilizer that exhibit favorable pharmacokinetics.

Disclosed is a pharmaceutical composition comprising about 4 mg of Fesoterodine and a stabilizer, preferably a sugar alcohol such as xylitol or sorbitol, which pharmaceutical composition exhibits the following parameters upon once-daily administration:

(a) a $C_{max}$ of about 2.19±0.66 ng/mL, a $t_{max}$ of about 5.17±0.75 hr, and an $AUC_{0-24}$ of about 17.99±7.16 hr*ng/mL on day one after the start of administration;

(b) a $C_{max}$ of about 1.92±0.84 ng/mL, a $t_{max}$ of about 5.67±0.82 hr, and an $AUC_{0-24}$ of about 21.39±9.60 hr*ng/mL on day two after the start of administration; and/or (c) a $C_{max}$ of about 2.12±1.28 ng/mL, a $t_{max}$ of about 4.17±2.04 hr, and an $AUC_{0-24}$ of about 20.26±11.44 hr*ng/mL on day three after the start of administration.

Also disclosed is a method of treatment for overactive bladder or related conditions comprising administering a pharmaceutical composition comprising about 4 mg of Fesoterodine and a stabilizer, preferably a sugar alcohol such as xylitol or sorbitol, which pharmaceutical composition exhibits the following parameters upon once-daily administration:

(a) a $C_{max}$ of about 2.19±0.66 ng/mL, a $t_{max}$ of about 5.17±0.75 hr, and an $AUC_{0-24}$ of about 17.99±7.16 hr*ng/mL on day one after the start of administration;

(b) a $C_{max}$ of about 1.92±0.84 ng/mL, a $t_{max}$ of about 5.67±0.82 hr, and an $AUC_{0-24}$ of about 21.39±9.60 hr*ng/mL on day two after the start of administration; and/or (c) a $C_{max}$ of about 2.12±1.28 ng/mL, a $t_{max}$ of about 4.17±2.04 hr, and an $AUC_{0-24}$ of about 20.26±11.44 hr*ng/mL on day three after the start of administration.

In certain embodiments, the method described immediately above does not lead to a significant increase in QTcF or QTcI. In certain embodiments, the method leads to a mean time average QTcF or QTcI decrease of about 4.6 ms to about 5.0 ms after three days of treatment.

Also disclosed is a pharmaceutical composition comprising about 4 mg of Fesoterodine and a stabilizer, preferably a sugar alcohol such as xylitol or sorbitol, which pharmaceutical composition exhibits the following parameters when the pharmaceutical composition is administered two times per day, the two administrations occurring at the same time:
(a) a $C_{max}$ of about 4.31±1.79 ng/mL, a $t_{max}$ of about 4.83±0.76 hr, and an $AUC_{0-24}$ of about 44.48±17.47 hr*ng/mL on day one after the start of administration;
(b) a $C_{max}$ of about 3.73±1.35 ng/mL, a $t_{max}$ of about 5.67±0.62 hr, and an $AUC_{0-24}$ of about 44.62±17.00 hr*ng/mL on day two after the start of administration; and/or
(c) a $C_{max}$ of about 5.15±2.02 ng/mL, a $t_{max}$ of about 5.00 hr, and an $AUC_{0-24}$ of about 52.03±21.76 hr*ng/mL on day three after the start of administration.

Also disclosed is a pharmaceutical composition comprising about 4 mg of Fesoterodine and a stabilizer, preferably a sugar alcohol such as xylitol or sorbitol, which pharmaceutical composition exhibits the following parameters when the pharmaceutical composition is administered three times per day, the three administrations occurring at the same time:
(a) a $C_{max}$ of about 6.88±3.21 ng/mL, a $t_{max}$ of about 5.00 hr, and an $AUC_{0-24}$ of about 61.81±18.43 hr*ng/mL on day one after the start of administration;
(b) a $C_{max}$ of about 6.63±1.59 ng/mL, a $t_{max}$ of about 5.67±0.82 hr, and an $AUC_{0-24}$ of about 63.97±16.11 hr*ng/mL on day two after the start of administration; and/or
(c) a $C_{max}$ of about 7.11±3.01 ng/mL, a $t_{max}$ of about 5.67±1.21 hr, and an $AUC_{0-24}$ of about 72.87±25.37 hr*ng/mL on day three after the start of administration.

Also disclosed is a pharmaceutical composition comprising about 4 mg of Fesoterodine and a stabilizer, preferably a sugar alcohol such as xylitol or sorbitol, which pharmaceutical composition exhibits the following parameters when the pharmaceutical composition is administered five times per day, the five administrations occurring at the same time:
(a) a $C_{max}$ of about 12.36±6.07 ng/mL, a $t_{max}$ of about 5.50±0.55 hr, and an $AUC_{0-24}$ of about 126±49 hr*ng/mL on day one after the start of administration;
(b) a $C_{max}$ of about 12.01±5.86 ng/mL, a $t_{max}$ of about 5.67±0.82 hr, and an $AUC_{0-24}$ of about 126±60.42 hr*ng/mL on day two after the start of administration; and/or
(c) a $C_{max}$ of about 13.25±7.26 ng/mL, a $t_{max}$ of about 5.33±0.52 hr, and an $AUC_{0-24}$ of about 136±68.76 hr*ng/mL on day three after the start of administration.

Also disclosed is a pharmaceutical composition comprising about 4 mg of Fesoterodine and a stabilizer, preferably a sugar alcohol such as xylitol or sorbitol, which pharmaceutical composition exhibits the following parameters when the pharmaceutical composition is administered seven times per day, the seven administrations occurring at the same time:
(a) a $C_{max}$ of about 16.29±5.69 ng/mL, a $t_{max}$ of about 5.50±0.55 hr, and an $AUC_{0-24}$ of about 181±59.74 hr*ng/mL on day one after the start of administration;
(b) a $C_{max}$ of about 18.14±3.57 ng/mL, a $t_{max}$ of about 6.00 hr, and an $AUC_{0-24}$ of about 204±50.74 hr*ng/mL on day two after the start of administration; and/or
(c) a $C_{max}$ of about 18.28±6.31 ng/mL, a $t_{max}$ of about 5.17±0.41 hr, and an $AUC_{0-24}$ of about 213±73.26 hr*ng/mL on day three after the start of administration.

Also disclosed is a pharmaceutical composition comprising about 8 mg of Fesoterodine and a stabilizer, preferably a sugar alcohol such as xylitol or sorbitol, which pharmaceutical composition exhibits the following parameters upon once-daily administration:
(a) a $C_{max}$ of about 4.31±1.79 ng/mL, a $t_{max}$ of about 4.83±0.76 hr, and an $AUC_{0-24}$ of about 44.48±17.47 hr*ng/mL on day one after the start of administration;
(b) a $C_{max}$ of about 3.73±1.35 ng/mL, a $t_{max}$ of about 5.67±0.62 hr, and an $AUC_{0-24}$ of about 44.62±17.00 hr*ng/mL on day two after the start of administration; and/or
(c) a $C_{max}$ of about 5.15±2.02 ng/mL, a $t_{max}$ of about 5.00 hr, and an $AUC_{0-24}$ of about 52.03±21.76 hr*ng/mL on day three after the start of administration.

Also disclosed is a method of treatment for overactive bladder or related conditions comprising administering to a patient in need thereof a pharmaceutical composition comprising about 8 mg of Fesoterodine and a stabilizer, preferably a sugar alcohol such as xylitol or sorbitol, which pharmaceutical composition exhibits the following parameters upon once-daily administration:
(a) a $C_{max}$ of about 4.31±1.79 ng/mL, a $t_{max}$ of about 4.83±0.76 hr, and an $AUC_{0-24}$ of about 44.48±17.47 hr*ng/mL on day one after the start of administration;
(b) a $C_{max}$ of about 3.73±1.35 ng/mL, a $t_{max}$ of about 5.67±0.62 hr, and an $AUC_{0-24}$ of about 44.62±17.00 hr*ng/mL on day two after the start of administration; and/or
(c) a $C_{max}$ of about 5.15±2.02 ng/mL, a $t_{max}$ of about 5.00 hr, and an $AUC_{0-24}$ of about 52.03±21.76 hr*ng/mL on day three after the start of administration.

In certain embodiments, the method described immediately above does not lead to a significant increase in QTcF or QTcI. In certain embodiments, the method leads to a mean time average QTcF or QTcI decrease of about 4.6 ms to about 5.0 ms after three days of treatment.

Also disclosed is a pharmaceutical composition comprising about 12 mg of Fesoterodine and a stabilizer, preferably a sugar alcohol such as xylitol or sorbitol, which pharmaceutical composition exhibits the following parameters upon once-daily administration:
(a) a $C_{max}$ of about 6.88±3.21 ng/mL, a $t_{max}$ of about 5.00 hr, and an $AUC_{0-24}$ of about 61.81±18.43 hr*ng/mL on day one after the start of administration;
(b) a $C_{max}$ of about 6.63±1.59 ng/mL, a $t_{max}$ of about 5.67±0.82 hr, and an $AUC_{0-24}$ of about 63.97±16.11 hr*ng/mL on day two after the start of administration; and/or
(c) a $C_{max}$ of about 7.11±3.01 ng/mL, a $t_{max}$ of about 5.67±1.21 hr, and an $AUC_{0-24}$ of about 72.87±25.37 hr*ng/mL on day three after the start of administration.

Also disclosed is a method of treatment for overactive bladder or related conditions comprising administering to a patient in need thereof a pharmaceutical composition comprising about 12 mg of Fesoterodine and a stabilizer, preferably a sugar alcohol such as xylitol or sorbitol, which pharmaceutical composition exhibits the following parameters upon once-daily administration:
(a) a $C_{max}$ of about 6.88±3.21 ng/mL, a $t_{max}$ of about 5.00 hr, and an $AUC_{0-24}$ of about 61.81±18.43 hr*ng/mL on day one after the start of administration;
(b) a $C_{max}$ of about 6.63±1.59 ng/mL, a $t_{max}$ of about 5.67±0.82 hr, and an $AUC_{0-24}$ of about 63.97±16.11 hr*ng/mL on day two after the start of administration; and/or
(c) a $C_{max}$ of about 7.11±3.01 ng/mL, a $t_{max}$ of about 5.67±1.21 hr, and an $AUC_{0-24}$ of about 72.87±25.37 hr*ng/mL on day three after the start of administration.

In certain embodiments, the method described immediately above does not lead to a significant increase in QTcF or QTcI. In certain embodiments, the method leads to a mean time average QTcF or QTcI decrease of about 4.6 ms to about 5.0 ms after three days of treatment.

Also disclosed is a pharmaceutical composition comprising about 20 mg of Fesoterodine and a stabilizer, preferably a sugar alcohol such as xylitol or sorbitol, which pharmaceutical composition exhibits the following parameters upon once-daily administration:
(a) a $C_{max}$ of about 12.36±6.07 ng/mL, a $t_{max}$ of about 5.50±0.55 hr, and an $AUC_{0-24}$ of about 126±49 hr*ng/mL on day one after the start of administration;

(b) a $C_{max}$ of about 12.01±5.86 ng/mL, a $t_{max}$ of about 5.67±0.82 hr, and an $AUC_{0-24}$ of about 126±60.42 hr*ng/mL on day two after the start of administration; and/or (c) a $C_{max}$ of about 13.25±7.26 ng/mL, a $t_{max}$ of about 5.33±0.52 hr, and an $AUC_{0-24}$ of about 136±68.76 hr*ng/mL on day three after the start of administration.

Also disclosed is a method of treatment for overactive bladder or related conditions comprising administering to a patient in need thereof a pharmaceutical composition comprising about 20 mg of Fesoterodine and a stabilizer, preferably a sugar alcohol such as xylitol or sorbitol, which pharmaceutical composition exhibits the following parameters upon once-daily administration:

(a) a $C_{max}$ of about 12.36±6.07 ng/mL, a $t_{max}$ of about 5.50±0.55 hr, and an $AUC_{0-24}$ of about 126±49 hr*ng/mL on day one after the start of administration;

(b) a $C_{max}$ of about 12.01±5.86 ng/mL, a $t_{max}$ of about 5.67±0.82 hr, and an $AUC_{0-24}$ of about 126±60.42 hr*ng/mL on day two after the start of administration; and/or (c) a $C_{max}$ of about 13.25±7.26 ng/mL, a $t_{max}$ of about 5.33±0.52 hr, and an $AUC_{0-24}$ of about 136±68.76 hr*ng/mL on day three after the start of administration.

In certain embodiments, the method described immediately above does not lead to a significant increase in QTcF or QTcI. In certain embodiments, the method leads to a mean time average QTcF or QTcI decrease of about 4.6 ms to about 5.0 ms after three days of treatment.

Also disclosed is a pharmaceutical composition comprising about 28 mg of Fesoterodine and a stabilizer, preferably a sugar alcohol such as xylitol or sorbitol, which pharmaceutical composition exhibits the following parameters upon once-daily administration:

(a) a $C_{max}$ of about 16.29±5.69 ng/mL, a $t_{max}$ of about 5.50±0.55 hr, and an $AUC_{0-24}$ of about 181±59.74 hr*ng/mL on day one after the start of administration;

(b) a $C_{max}$ of about 18.14±3.57 ng/mL, a $t_{max}$ of about 6.00 hr, and an $AUC_{0-24}$ of about 204±50.74 hr*ng/mL on day two after the start of administration; and/or (c) a $C_{max}$ of about 18.28±6.31 ng/mL, a $t_{max}$ of about 5.17±0.41 hr, and an $AUC_{0-24}$ of about 213±73.26 hr*ng/mL on day three after the start of administration.

Also disclosed is a method of treatment for overactive bladder or related conditions comprising administering to a patient in need thereof a pharmaceutical composition comprising about 28 mg of Fesoterodine and a stabilizer, preferably a sugar alcohol such as xylitol or sorbitol, which pharmaceutical composition exhibits the following parameters upon once-daily administration:

(a) a $C_{max}$ of about 16.29±5.69 ng/mL, a $t_{max}$ of about 5.50±0.55 hr, and an $AUC_{0-24}$ of about 181±59.74 hr*ng/mL on day one after the start of administration;

(b) a $C_{max}$ of about 18.14±3.57 ng/mL, a $t_{max}$ of about 6.00 hr, and an $AUC_{0-24}$ of about 204±50.74 hr*ng/mL on day two after the start of administration; and/or (c) a $C_{max}$ of about 18.28±6.31 ng/mL, a $t_{max}$ of about 5.17±0.41 hr, and an $AUC_{0-24}$ of about 213±73.26 hr*ng/mL on day three after the start of administration.

In certain embodiments, the method described immediately above does not lead to a significant increase in QTcF or QTcI. In certain embodiments, the method leads to a mean time average QTcF or QTcI decrease of about 4.6 ms to about 5.0 ms after three days of treatment.

DETAILED DESCRIPTION

Figure 1A:
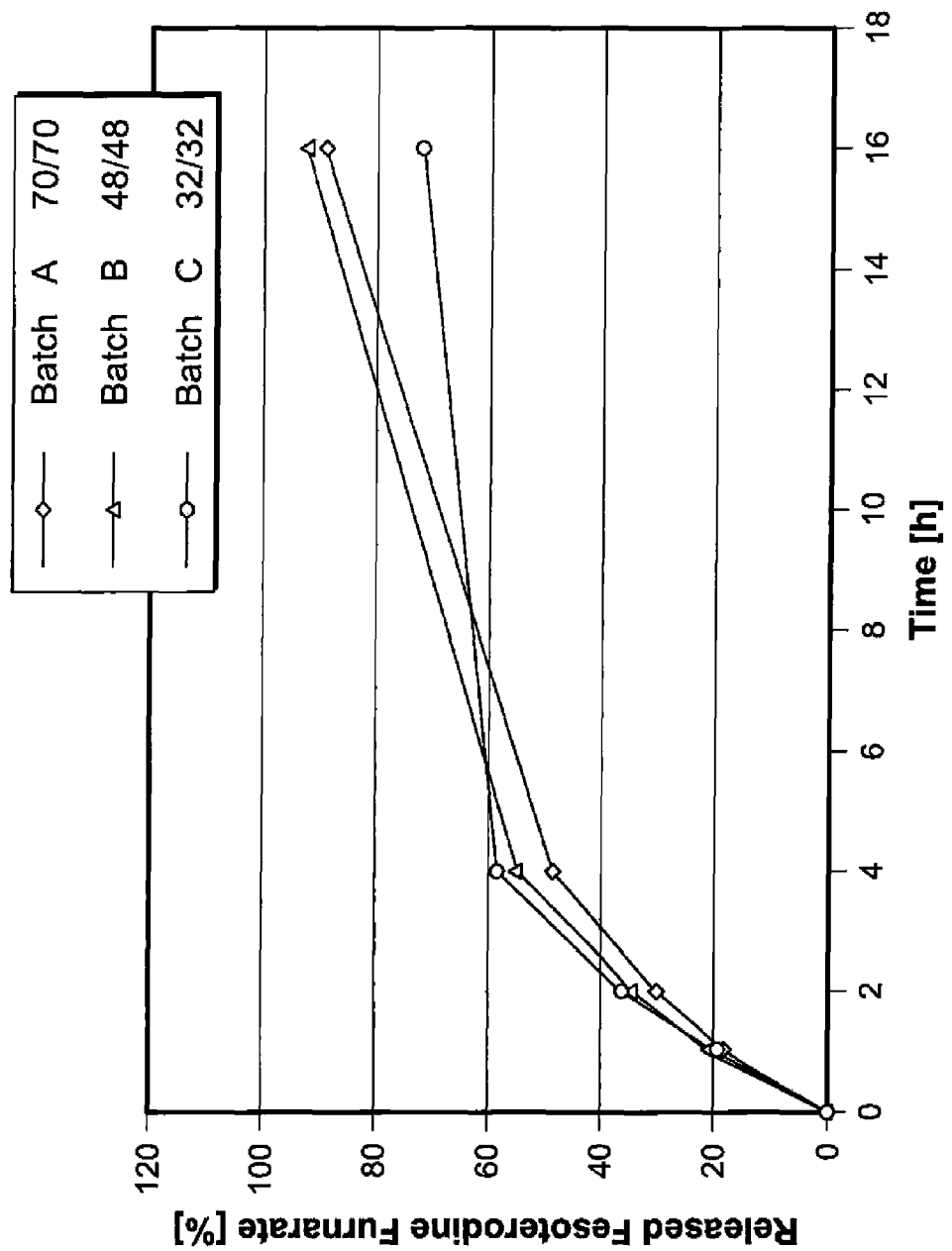
FIG. 1 shows the in vitro dissolution profiles of Fesoterodine-containing pharmaceutical compositions (A) based on a 4 mg tablet and (B) based on an 8 mg tablet.
Figure 1B:
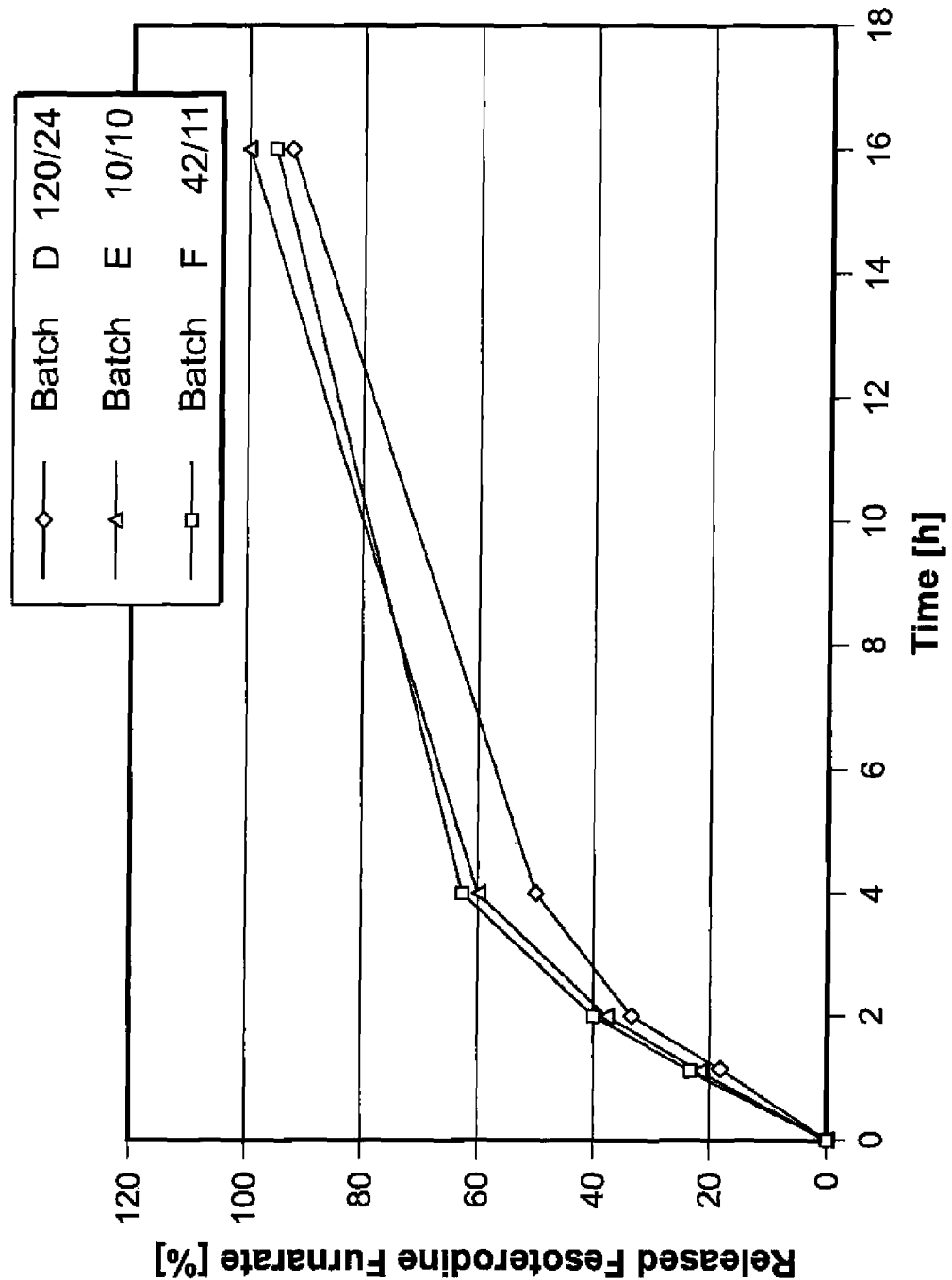

Unless the content indicates otherwise, the term "Fesoterodine" includes pharmaceutically acceptable solvates of 2-[(1R)-3-(diisopropylamino)-1-phenylpropyl]-4-(hydroxymethyl)phenyl isobutyrate (formula I), particularly hydrates of Fesoterodine. "Fesoterodine" also includes pharmaceutically acceptable salts of 2-[(1R)-3-(diisopropylamino)-1-phenylpropyl]-4-(hydroxymethyl)phenyl isobutyrate (formula I), particularly the hydrogen fumarate salt, as well as the free base.

Throughout this application, amounts indicated relate to Fesoterodine in the form which is used, i.e., either the free base or the salt.

Fesoterodine is an ester which is susceptible to hydrolyzation after administration in vivo as well as during storage under stress conditions to give a main product (2-[(1R)-3-(diisopropylamino)-1-phenylpropyl]-4-(hydroxymethyl)phenol) (formula II), which is referred to herein as the "Active Metabolite" and corresponds to the following structure:

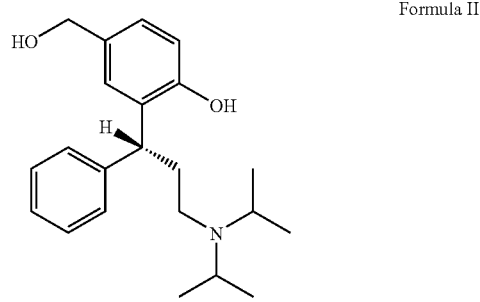

Formula II

Throughout this application the term "hydrolyzation product" refers to the Active Metabolite of formula II. Other degradation products also may result from the metabolism and/or degradation of Fesoterodine. As used herein, "total degradation products" will include, at least in part, hydrolyzation product.

"Stabilizer," as the term is used herein, means a substance, particularly a pharmaceutically acceptable excipient, which inhibits, prevents, slows down, or reduces the degradation of Fesoterodine as compared to Fesoterodine in the absence of the substance. As used herein, the term "stabilizer" also embraces a combination of two or more of the stabilizers according to the invention. By way of example, a combination of xylitol and sorbitol, or a combination of xylitol, sorbitol and polydextrose, or a combination of xylitol and polydextrose may be mentioned.

Whether a substance is a stabilizer can be determined by the following procedure: about 10 g. of a mixture of Fesoterodine and a substance suspected to be a stabilizer in a ratio of about 1:9 (by weight) is manually crushed with a pestle and then stored for about 6 weeks in an open vial at about 40° C. and about 75% relative humidity. A substance is a stabilizer if the purity of Fesoterodine in the mixture with the substance is higher under the above storage conditions than the purity of Fesoterodine that was stored in the absence of the substance.

The value of Fesoterodine purity, as well as the relative amounts of hydrolyzation product and total degradation products given, are determined via HPLC by the area-% method. In this area-% method the purity is determined by comparing the area of the respective HPLC peaks with the total area of all signals in the HPLC profile that can be related to Fesoterodine and its hydrolyzation and/or degradation products.

Whether a certain excipient is suitable as a stabilizer according to the present invention can also for example be determined by the following method:

At first a granulate is prepared:

1 mass equivalent Fesoterodine or a salt thereof, preferably Fesoterodine hydrogen fumarate, and 9 mass equivalents of the excipient are weighed separately. If the excipient is agglomerated, it is passed through a sieve (1.5 mm).

Fesoterodine and the excipient are passed through a sieve (0.8 mm).

The fesoterodine and the excipient are transferred into a suitable granulator (e.g., a high-shear mixer granulator such as those manufactured by Lödige, Type Diosna P1/6) at a temperature of below about 35° C. and mixed for 1 minute.

About 5.5 wt % of purified water is added to the dry mixture while stirring.

The mixture is stirred with a chopper for about 90 to 120 seconds.

The mixer is emptied, and the contents are transferred to a sieving machine to form a wet granulate, which then is passed through a sieve or a screen (4.0 mm).

The sieved granulate is dried on trays at about 45° C. for a minimum of 8 h. in a drying chamber/oven until a water content of not more than about 0.5%.

The dried granulate is passed through a sieve (0.5 to 1.0 mm).

The dried granulate is then mixed (at a speed of about 8 rpm) for 5 minutes.

One part of the granulate is examined to determine the initial amount of hydrolyzation and degradation product, while another part is stored in open vials as described above and subsequently examined to determine the final amount of hydrolyzation and degradation product.

Batches of this granulate are then stored under three conditions, respectively, as follows:
a) 25° C. and 60% r.H. in closed vials for 6 weeks
b) 40° C. and 75% r.H. in closed vials for 6 weeks
c) 40° C. and 75% r.H. in open vials for 6 weeks The content of the active metabolite of Formula II is determined via HPLC by the area-% method. In this area-% method, the amount of active metabolite is determined by comparing the area of the respective HPLC peak with the total area of all signals in the HPLC profile that can be related to fesoterodine and its hydrolyzation and/or degradation products.

According to this procedure, a substance is a stabilizer if it limits the formation of Active Metabolite of Formula II during storage under at least two of the above conditions as follows:
a) about 1 wt % or less, preferably 0.5 wt % or less, and particularly preferably 0.36 wt % or less
b) about 2 wt % or less, preferably 1 wt % or less, and particularly preferably 0.5 wt % or less
c) about 2 wt % or less, preferably 1.5 wt % or less, and particularly preferably 0.58 wt % or less.

In preferred embodiments, stabilizers prevent the degradation of Fesoterodine to the extent that if a stabilizer is mixed with Fesoterodine and stored for about 6 weeks at about 40° C. and about 75% relative humidity in open vials, the difference ($P_{F+S}-P_F$) between the Fesoterodine purity in the mixture with a stabilizer ($P_{F+S}$) and the Fesoterodine purity upon storage of Fesoterodine alone ($P_F$) is at least about 1%, preferably at least about 1.5%, and more preferably at least about 2%.

Other preferred stabilizers are those that inhibit, prevent, slow down, or reduce the degradation of Fesoterodine during the production and storage of a granulate. Such a preferred stabilizer can be determined by producing about 10 g. of a granulate of Fesoterodine and a substance suspected to be a stabilizer in a ratio of about 1:9 (by weight) under the conditions as described below, storing the granulate in an open vial at about 40° C., about 75% relative humidity (r.H.) for about 6 weeks and measuring the relative amount of the total hydrolyzation and degradation products via HPLC by the area % method under the conditions as described in Example 6b and above. An excipient is a preferred stabilizer if the difference ($D_F-D_O$) between the final amount of total hydrolyzation and degradation products after about 6 weeks of storage in an open vial at about 40° C., about 75% relative humidity (r.H.) ($D_F$) and the initial amount of hydrolyzation and degradation products after the production of the granulate ($D_O$) is less than about 3%, preferably less than about 2%, or more preferably even less than about 1.5%.

Stabilizers of the present invention include, but are not limited to, sorbitol, xylitol, polydextrose, isomalt, dextrose, and combinations thereof. Preferred stabilizers include sugar alcohols meeting the aforementioned criteria and more specifically include, but are not limited to, xylitol and sorbitol. Xylitol is one preferred stabilizer.

The ratio of the Fesoterodine to the stabilizer is preferably between about 1%-20% (w/w) and, more preferably, between about 5% and about 10% (w/w).

Particularly preferred are those stabilizers that are capable of reducing the destabilizing effect of certain other excipients, such as, e.g., lactose, on Fesoterodine.

Stabilizers may be added to the matrix of a suitable formulation, or preferably can be used in granulates, optionally together with one or more other excipients.

Granulates comprising Fesoterodine or a pharmaceutically acceptable salt or solvate thereof and a stabilizer, and optionally further excipients, can be formed by mixing the components either dry or, preferably, with a liquid, e.g., with water, and then granulating the mixture.

A "pharmaceutically acceptable stabilizer" is a stabilizer which is not biologically or otherwise undesirable, i.e., the stabilizer can be administered to an individual without causing significant undesirable biological effects or interacting in a deleterious manner with any of the components of the composition in which it is contained.

In a preferred embodiment, the stabilizers disclosed herein inhibit, prevent, slow down, or reduce the hydrolyzation of Fesoterodine into Active Metabolite of formula (II). Thus, in one aspect, disclosed are compositions, mixtures, granulates and other pharmaceutical compositions comprising Fesoterodine and a stabilizer, wherein the Fesoterodine is protected against hydrolyzation under various stress conditions (see, e.g., Table 6 and Table 7).

The stabilizers of the present invention can also inhibit, prevent, slow down, or reduce the degradation of further ester compounds that are susceptible to hydrolysis. In particular, stabilizers of the present invention are useful for the stabilization of esters of the Active Metabolite of fesoterodine of Formula II.

Thus, another aspect of this invention relates to the use of a substance selected from the group consisting of xylitol, sorbitol, polydextrose, isomalt, and dextrose for the stabilization of a pharmaceutical composition comprising as active ingredient an ester compound that is susceptible to hydrolysis, particularly an ester of the Active Metabolite of Fesoterodine of Formula II and preferably such an ester as indicated below, or a pharmaceutically acceptable salt or solvate thereof.

Esters of the Active Metabolite of Fesoterodine of Formula II that can be stabilized in this way include the following compounds:

a) Phenolic Monoesters of Formula III

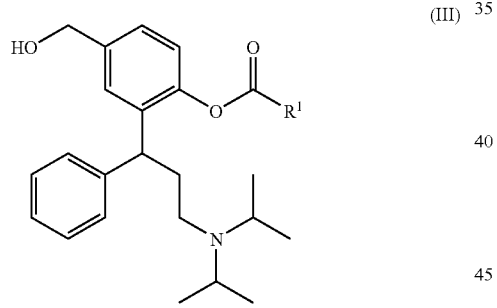

(III)

wherein $R^1$ is $C_1$-$C_6$ alkyl or phenyl;

b) Identical Diesters of Formula IV

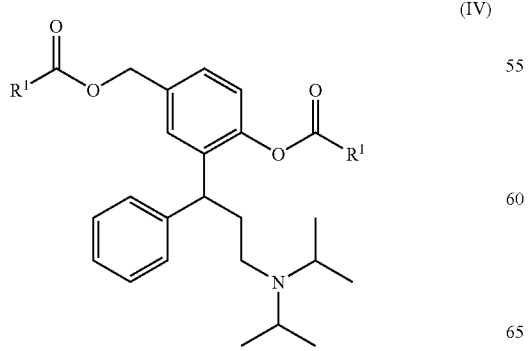

(IV)

wherein each $R^1$ is as defined above;

c) Mixed Diesters of Formula V

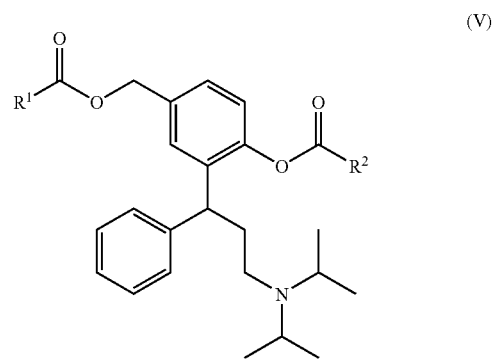

(V)

wherein $R^1$ is as defined above, $R^2$ is hydrogen, $C_1$-$C_6$ alkyl or phenyl with the proviso that $R^1$ and $R^2$ are different;

d) Benzylic Monoesters of Formula VI

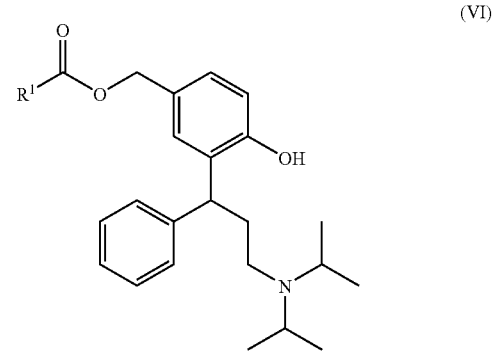

(VI)

wherein $R^1$ is as defined above;

e) Intramolecular Cyclic Diesters of Formula VII and Formula VIII

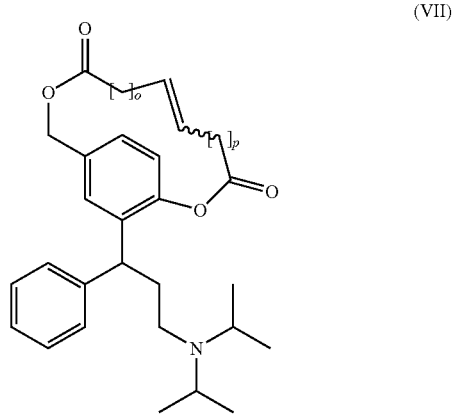

(VII)

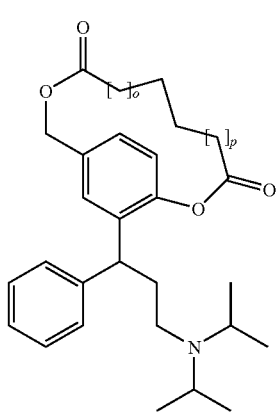

(VIII)

wherein o and p are the same or different and represent the number of methylene units —(CH$_2$)— and may range from 0 to 6; and f) Inorganic Esters Such as (±)-Benzoic acid 2-(3-isopropylamino-1-phenylpropyl)-4-sulphooxymethyl-phenyl ester;

and their salts with physiologically acceptable acids, their free bases and, when the compounds can be in the form of optical isomers, the racemic mixture and the individual enantiomers.

In yet another aspect, disclosed also is a pharmaceutical composition comprising such an ester as defined above, or a pharmaceutically acceptable salt or solvate thereof, and a pharmaceutically acceptable stabilizer, wherein said stabilizer is selected from the group consisting of xylitol, sorbitol, polydextrose, isomalt, dextrose and combinations thereof.

Preferred pharmaceutical compositions are those comprising (a) a phenolic monoester of Formula III as defined above, particularly preferably a phenolic monoester wherein $R^1$ is a linear or branched $C_3$-$C_6$ alkyl, or a pharmaceutically acceptable salt or solvate thereof, and (b) a pharmaceutically acceptable stabilizer, wherein said stabilizer is selected from the group consisting of xylitol, sorbitol, polydextrose, isomalt, dextrose and combinations thereof.

In one aspect of the present invention, the pharmaceutical composition comprising the ester as described above, preferably the phenolic monoester of Formula III, and the stabilizer, contains said ester in the form of a salt, preferably a salt of a di- or tricarboxylic acid, or a partially hydrogenated di- or tricarboxylic acid, wherein said salt of said ester has an auto pH in water that is close to the pH stability optimum of the respective ester, for example at about pH 3-5.

In another embodiment, provided are various compositions comprising Fesoterodine and a stabilizer. Exemplary, non-exhaustive examples of various compositions may be described as follows.

A pharmaceutical composition comprising Fesoterodine and a stabilizer, wherein the Fesoterodine is stable against degradation at about 40° C., about 75% r.H. in an open vial such that after about 6 weeks at about 40° C., about 75% r.H. in an open vial, the pharmaceutical composition contains no more than about 7%, about 6%, about 5%, about 4.9%, about 4.8%, about 4.7%, about 4.6%, about 4.5%, or about 4.4% of Active Metabolite of Formula II.

A pharmaceutical composition comprising Fesoterodine and a stabilizer, wherein the Fesoterodine is stable against degradation at about 40° C., 75% r.H. in a closed vial such that after about 6 weeks at about 40° C., 75% r.H. in closed vial the pharmaceutical composition contains no more than about 2.5%, about 2.2%, about 2.1%, about 2%, about 1.9%, about 1.8%, about 1.7%, about 1.6%, about 1.5%, about 1.4%, about 1.3%, about 1.2%, about 1.1%, or about 1% of Active Metabolite of formula (II). More preferably, such a pharmaceutical composition contains no more than about 1.09% of Active Metabolite of Formula II after storage under such conditions.

A pharmaceutical composition comprising Fesoterodine and a stabilizer wherein Fesoterodine is stable against degradation at about 40° C., 75% r.H. in an open vial such that after about 12 weeks at about 40° C., 75% r.H. in open vial the pharmaceutical composition contains at least about 85%, about 86%, about 87%, about 88%, about 89% or about 90% Fesoterodine. More preferably, such a pharmaceutical composition contains at least about 89% of Fesoterodine after storage under such conditions.

A pharmaceutical composition comprising Fesoterodine and a stabilizer wherein Fesoterodine is stable against degradation at about 25° C., about 60% r.H. in a closed vial such that after about 6 weeks at about 25° C., about 60% r.H. in closed vial the pharmaceutical composition contains no more than about 1%, about 0.9%, about 0.8%, about 0.7%, about 0.6%, about 0.5%, about 0.4%, about 0.3%, about 0.2%, or about 0.1% of Active Metabolite. More preferably, such a pharmaceutical composition contains no more than about 0.18% of Active Metabolite of Formula II after storage under such conditions.

In another embodiment, the pharmaceutical composition for the oral administration of Fesoterodine or a pharmaceutically acceptable salt thereof comprises Fesoterodine and at least one stabilizer selected from the group consisting of sorbitol, xylitol, polydextrose, isomalt, dextrose, and combinations thereof, preferably a stabilizing sugar alcohol, including a sugar alcohol chosen from xylitol and sorbitol. The composition may include one or more further excipients.

At least one of the further excipients that may be included is a sustained release agent, preferably a substituted cellulose derivative, such as hydroxypropylmethyl cellulose (HPMC). The sustained release agent, e.g. HPMC, facilitates the delayed release of Fesoterodine from the formulation such that the formulation can be administered to a patient less often, such as once daily.

Another embodiment is a pharmaceutical composition for the oral administration of Fesoterodine or a pharmaceutically acceptable salt thereof that is a granulate of Fesoterodine and at least one suitable excipient, preferably a stabilizer selected from the group consisting of sorbitol, xylitol, polydextrose, isomalt, dextrose, and combinations thereof, and even more preferably a sugar alcohol chosen from xylitol and sorbitol.

In another embodiment is a pharmaceutical composition for the oral administration of Fesoterodine or a pharmaceutically acceptable salt thereof that comprises granulate(s) of Fesoterodine and at least one suitable excipient, preferably a stabilizer selected from the group consisting of sorbitol, xylitol, polydextrose, isomalt, dextrose, and combinations thereof, and even more preferably a sugar alcohol chosen from xylitol and sorbitol. Optionally, at least one further excipient may be included in such compositions.

Another embodiment is a pharmaceutical composition for the oral administration of Fesoterodine or a pharmaceutically acceptable salt thereof that can be produced by a method comprising wet granulating Fesoterodine and at least one suitable excipient, preferably a stabilizer selected from the group consisting of sorbitol, xylitol, polydextrose, isomalt, dextrose, and combinations thereof, and even more preferably a sugar alcohol chosen from xylitol and sorbitol to form a granulate, and optionally mixing the granulate with further excipients, such as for example one or more types of HPMC.

A pharmaceutical composition made from Fesoterodine granulate described herein was found to have about 90% of the original amount of Fesoterodine remaining in undegraded form. (See Table 4).

The following exemplary, non-exhaustive examples of pharmaceutical compositions made from granulates of Fesoterodine are thus described.

In further additional embodiments, the stabilizer used in pharmaceutical compositions made from a granulate of Fesoterodine can be xylitol. Thus, exemplary, non-exhaustive examples of such compositions include the following.

A pharmaceutical composition comprising Fesoterodine and xylitol, wherein the Fesoterodine in the pharmaceutical composition is stable against degradation at about 40° C., about 75% r.H. in a closed vial such that after about 6 weeks at about 40° C., about 75% r.H. in a closed vial the pharmaceutical composition contains no more than about 2%, about 1.9%, about 1.8%, about 1.7%, about 1.6%, about 1.5%, about 1.4%, about 1.3%, about 1.2%, about 1.1%, or about 1% of Active Metabolite of Formula II. More preferably, such a pharmaceutical composition contains no more than about 1.09% of Active Metabolite of Formula II after storage under such conditions.

Also provided is a pharmaceutical composition comprising Fesoterodine and xylitol, wherein the Fesoterodine in the pharmaceutical composition is stable against degradation at about 40° C., about 75% r.H. in an open vial such that after about 6 weeks at about 40° C., about 75% r.H. in an open vial the pharmaceutical composition contains no more than about 5%, about 4.9%, about 4.8%, about 4.7%, about 4.6%, about 4.5%, or about 4.4% of Active Metabolite of Formula II.

A pharmaceutical composition comprising Fesoterodine and xylitol, wherein the Fesoterodine in the pharmaceutical composition is stable against degradation at about 40° C., about 75% r.H. in a closed vial such that after about 6 weeks at about 40° C., about 75% r.H. in a closed vial the pharmaceutical composition contains no more than about 2%, about 1.9%, about 1.8%, about 1.7%, about 1.6%, or about 1.5% of total degradation products of Fesoterodine. More preferably, such a pharmaceutical composition contains no more than about 1.54% of total hydrolyzation and degradation products of Fesoterodine after storage under such conditions.

A pharmaceutical composition comprising Fesoterodine and xylitol, wherein the Fesoterodine in the pharmaceutical composition is stable against degradation at about 40° C., about 75% r.H. in an open vial such that after about 6 weeks at about 40° C., about 75% r.H. in an open vial the pharmaceutical composition contains no more than about 7%, about 6.9%, about 6.8%, or about 6.7% of total degradation products of Fesoterodine. More preferably, such a pharmaceutical composition contains no more than about 6.78% of total hydrolyzation and degradation products of Fesoterodine after storage under such conditions.

A pharmaceutical composition comprising Fesoterodine and xylitol wherein the Fesoterodine in the pharmaceutical composition is stable against degradation at about 40° C., about 75% r.H. in an open vial such that after about 12 weeks at about 40° C., about 75% r.H. in an open vial at least about 80%, about 85%, about 90%, or about 95% of the original amount of Fesoterodine in the composition remains, i.e., is undegraded.

A pharmaceutical composition comprising Fesoterodine and xylitol, wherein the Fesoterodine in the pharmaceutical composition is stable against degradation at about 25° C., about 60% r.H. in a closed vial such that after about 6 weeks at about 25° C., about 60% r.H. in a closed vial the pharmaceutical composition contains no more than about 1%, about 0.9%, about 0.8%, about 0.7%, about 0.6%, about 0.5%, about 0.4%, about 0.3%, about 0.2%, or about 0.1% of Active Metabolite of Formula II. More preferably, such a pharmaceutical composition contains no more than about 0.18% of Active Metabolite of Formula II after storage under such conditions.

A pharmaceutical composition comprising Fesoterodine and xylitol, wherein the Fesoterodine in the pharmaceutical composition is stable against degradation at about 25° C., about 60% r.H. in a closed vial such that after about 6 weeks at about 25° C., about 60% r.H. in a closed vial the pharmaceutical composition contains no more than about 1%, about 0.9%, about 0.8%, about 0.7%, about 0.6%, about 0.5%, about 0.4%, or about 0.3% of total degradation products of Fesoterodine. More preferably, such a pharmaceutical composition contains no more than about 0.31% of total hydrolyzation and degradation products of Fesoterodine after storage under such conditions.

In further additional embodiments, the stabilizer used in pharmaceutical composition comprising Fesoterodine can be sorbitol. Thus, exemplary, non-exhaustive examples of such compositions include the following.

A pharmaceutical composition comprising Fesoterodine and sorbitol, wherein the Fesoterodine in the pharmaceutical composition is stable against degradation at about 40° C., about 75% r.H. in an open vial such that after about 6 weeks at about 40° C., about 75% r.H. in an open vial the pharmaceutical composition contains no more than about 7%, about 6.9%, about 6.8%, or about 6.7% of Active Metabolite of Formula II. More preferably, such a pharmaceutical composition contains no more than about 6.71% of Active Metabolite of Formula II after storage under such conditions.

A pharmaceutical composition comprising Fesoterodine and sorbitol, wherein the Fesoterodine in the pharmaceutical composition is stable against degradation at about 40° C., about 75% r.H. in a closed vial such that after about 6 weeks at about 40° C., about 75% r.H. in a closed vial the pharmaceutical composition contains no more than about 3%, about 2.9%, about 2.8%, about 2.7%, about 2.6%, about 2.5%, about 2.4%, about 2.3%, about 2.2%, or about 2.1% of Active Metabolite of Formula II. More preferably, such a pharmaceutical composition contains no more than about 2.14% of Active Metabolite of Formula II after storage under such conditions.

A pharmaceutical composition comprising Fesoterodine and sorbitol, wherein the Fesoterodine in the pharmaceutical composition is stable against degradation at about 40° C., about 75% r.H. in an open vial such that after about 6 weeks at about 40° C., about 75% r.H. in an open vial the pharmaceutical composition contains no more than about 11%, about 10.9%, about 10.8%, about 10.7%, about 10.6%, about 10.5%, or about 10.4% of total degradation products of Fesoterodine. More preferably, such a pharmaceutical composition contains no more than about 10.48% of total hydrolyzation and degradation products of Fesoterodine after storage under such conditions.

A pharmaceutical composition comprising Fesoterodine and sorbitol, wherein the Fesoterodine in the pharmaceutical composition is stable against degradation at about 40° C., about 75% r.H. in a closed vial such that after about 6 weeks at about 40° C., about 75% r.H. in a closed vial the pharmaceutical composition contains no more than about 4%, about 3.9%, about 3.8%, about 3.7%, or about 3.6% of total degradation products of Fesoterodine. More preferably, such a pharmaceutical composition contains no more than about 3.66% of total hydrolyzation and degradation products of Fesoterodine after storage under such conditions.

A pharmaceutical composition comprising Fesoterodine and sorbitol, wherein the Fesoterodine in the pharmaceutical composition is stable against degradation at about 25° C., about 60% r.H. in a closed vial such that after about 6 weeks at about 25° C., about 60% r.H. in a closed vial the pharmaceutical composition contains no more than about 1%, about 0.9%, about 0.8%, about 0.7%, about 0.6%, about 0.5%, about 0.4%, or about 0.3% of Active Metabolite of Formula II. More preferably, such a pharmaceutical composition contains no more than about 0.39% of Active Metabolite of Formula II after storage under such conditions.

A pharmaceutical composition comprising Fesoterodine and sorbitol, wherein the Fesoterodine in the pharmaceutical composition is stable against degradation at about 25° C., about 60% r.H. in a closed vial such that after about 6 weeks at about 25° C., about 60% r.H. in a closed vial the pharmaceutical composition contains no more than about 1%, about 0.9%, about 0.8%, about 0.7%, or about 0.6% of total degradation products of Fesoterodine. More preferably, such a pharmaceutical composition contains no more than about 0.64% of total hydrolyzation and degradation products of Fesoterodine after storage under such conditions.

In a further embodiment, provided is a granulate of Fesoterodine and at least one suitable excipient, preferably a stabilizer selected from the group consisting of sorbitol, xylitol, polydextrose, isomalt, dextrose, and combinations thereof, and even more preferably a sugar alcohol chosen from xylitol and sorbitol. Optionally, at least one further excipient may be included in such granulate.

Whereas Fesoterodine itself was found to have degraded after about 12 weeks at about 40° C., 75% relative humidity (r.H.) in open vials to the extent that only about 50% of the original Fesoterodine remained in undegraded form, a granulate of Fesoterodine and xylitol was found to have about 93% of the original amount of Fesoterodine remaining in undegraded form after about 12 weeks under the same conditions.

Thus, exemplary, non-exhaustive examples of Fesoterodine granulate are provided.

A granulate of Fesoterodine and a stabilizer such as xylitol, wherein the Fesoterodine in the granulate is stable against degradation at about 40° C., about 75% r.H. in an open vial such that after about 12 weeks at about 40° C., about 75% r.H. in an open vial at least about 80%, about 85%, about 90%, or about 95% of the original amount of Fesoterodine in the granulate remains, i.e., is undegraded.

A granulate of Fesoterodine and a stabilizer such as xylitol, wherein the Fesoterodine in the granulate is stable against degradation at about 40° C., about 75% r.H. in an open vial such that after about 6 weeks at about 40° C., about 75% r.H. in an open vial the granulate contains no more than about 1%, about 0.9%, about 0.8%, about 0.7%, about 0.6%, or about 0.5% of Active Metabolite of Formula II by weight. More preferably, such a granulate contains no more than about 0.58% of Active Metabolite of Formula II after storage under such conditions.

A granulate of Fesoterodine and a stabilizer such as xylitol wherein the Fesoterodine in the granulate is stable against degradation at about 40° C., about 75% r.H. in a closed vial such that after about 6 weeks at about 40° C., about 75% r.H. in a closed vial the granulate contains no more than about 1%, about 0.9%, about 0.8%, about 0.7%, about 0.6%, about 0.5%, about 0.4%, about 0.3%, or about 0.2% of Active Metabolite of Formula II. More preferably, such a granulate contains no more than about 0.23% of Active Metabolite of Formula II after storage under such conditions.

A granulate of Fesoterodine and a stabilizer such as xylitol, wherein the Fesoterodine in the granulate is stable against degradation at about 40° C., about 75% r.H. in an open vial such that after about 6 weeks at about 40° C., about 75% r.H. in an open vial the granulate contains no more than about 2%, about 1.9%, about 1.8%, about 1.7%, about 1.6%, about 1.5%, about 1.4%, about 1.3%, or about 1.2% of total degradation products of Fesoterodine. More preferably, such granulate contains no more than about 1.25% of total hydrolyzation and degradation products of Fesoterodine after storage under such conditions.

A granulate of Fesoterodine and a stabilizer, preferably xylitol, wherein the Fesoterodine in the granulate is stable against degradation at about 40° C., about 75% r.H. in a closed vial such that after about 6 weeks at about 40° C., about 75% r.H. in a closed vial the granulate contains no more than about 1%, about 0.9%, about 0.8%, about 0.7%, about 0.6%, about 0.5%, about 0.4%, or about 0.3% of total degradation products of Fesoterodine. More preferably, such granulate contains no more than about 0.37% of total hydrolyzation and degradation products of Fesoterodine after storage under such conditions.

A granulate of Fesoterodine and a stabilizer, preferably xylitol, wherein the Fesoterodine in the granulate is stable against degradation at about 25° C., about 60% r.H. in a closed vial such that after about 6 weeks at about 25° C., about 60% r.H. in a closed vial the granulate contains no more than about 1%, about 0.9%, about 0.8%, about 0.7%, about 0.6%, about 0.5%, about 0.4%, about 0.3%, about 0.2%, or about 0.1% of Active Metabolite of Formula II. More preferably, such a granulate contains no more than about 0.12% of Active Metabolite of Formula II after storage under such conditions.

A granulate of Fesoterodine and a stabilizer, preferably xylitol, wherein the Fesoterodine in the granulate is stable against degradation at about 25° C., about 60% r.H. in a closed vial such that after about 6 weeks at about 25° C., about 60% r.H. in a closed vial the granulate contains no more than about 1%, about 0.9%, about 0.8%, about 0.7%, about 0.6%, about 0.5%, about 0.4%, about 0.3%, or about 0.2% of total degradation products of Fesoterodine. More preferably, such a granulate contains no more than about 0.22% of total hydrolyzation and degradation products of Fesoterodine after storage under such conditions.

In further additional embodiments, the granulate includes sorbitol, polydextrose, isomalt, or dextrose as the stabilizer. Exemplary, non-exhaustive examples of such granulate include the following.

A granulate of Fesoterodine and sorbitol, wherein the Fesoterodine in the granulate is stable against degradation at about 40° C., about 75% r.H. in an open vial such that after about 6 weeks at about 40° C., about 75% r.H. in an open vial the granulate contains no more than about 1%, about 0.9%, about 0.8%, about 0.7%, about 0.6%, about 0.5%, or about 0.4% of Active Metabolite of Formula II. More preferably, such granulate contains no more than about 0.48% of Active Metabolite of Formula II after storage under such conditions.

A granulate of Fesoterodine and sorbitol, wherein the Fesoterodine in the granulate is stable against degradation at about 40° C., about 75% r.H. in a closed vial such that after about 6 weeks at about 40° C., about 75% r.H. in a closed vial the granulate contains no more than about 2%, about 1.9%, about 1.8%, about 1.7%, about 1.6%, about 1.5%, or about 1.4% of Active Metabolite of Formula II. More preferably, such granulate contains no more than about 1.47% of Active Metabolite of Formula II after storage under such conditions.

A granulate of Fesoterodine and sorbitol, wherein the Fesoterodine in the granulate is stable against degradation at about 40° C., about 75% r.H. in an open vial such that after about 6 weeks at about 40° C., about 75% r.H. in an open vial the granulate contains no more than about 2%, about 1.9%, about 1.8%, about 1.7%, about 1.6%, about 1.5%, about 1.4%, about 1.3%, about 1.2%, about 1.1%, about 1.0%, or about 0.9% of total degradation products of Fesoterodine. More preferably, such granulate contains no more than about 0.91% of total hydrolyzation and degradation products of Fesoterodine after storage under such conditions.

A granulate of Fesoterodine and sorbitol, wherein the Fesoterodine in the granulate is stable against degradation at about 40° C., about 75% r.H. in a closed vial such that after about 6 weeks at about 40° C., about 75% r.H. in a closed vial the granulate contains no more than about 3%, about 2.9%, about 2.8%, or about 2.7% of total degradation products of Fesoterodine. More preferably, such granulate contains no more than about 2.79% of total hydrolyzation and degradation products of Fesoterodine after storage under such conditions.

A granulate of Fesoterodine and sorbitol, wherein the Fesoterodine in the granulate is stable against degradation at about 25° C., about 60% r.H. in a closed vial such that after about 6 weeks at about 25° C., about 60% r.H. in a closed vial the granulate contains no more than about 1%, about 0.9%, about 0.8%, about 0.7%, about 0.6%, about 0.5%, about 0.4%, or about 0.3% of Active Metabolite of Formula II. More preferably, such granulate contains no more than about 0.36% of Active Metabolite of Formula II under such conditions.

A granulate of Fesoterodine and sorbitol, wherein the Fesoterodine in the granulate is stable against degradation at about 25° C., about 60% r.H. in a closed vial such that after about 6 weeks at about 25° C., about 60% r.H. in a closed vial the granulate contains no more than about 1%, about 0.9%, about 0.8%, about 0.7%, about 0.6%, or about 0.5% of total degradation products of Fesoterodine. More preferably, such granulate contains no more than about 0.51% of total hydrolyzation and degradation products of Fesoterodine after storage under such conditions.

The stability of Fesoterodine in pharmaceutical compositions comprising Fesoterodine and xylitol described herein has been tested for up to 24 months in closed containers at about 25° C., about 60% r.H. and found to be remarkably high. (See Table 3).

Accordingly, in another embodiment, provided is a pharmaceutical composition comprising Fesoterodine and xylitol wherein the Fesoterodine in the pharmaceutical composition is stable against degradation at about 25° C., about 60% r.H. in a closed vial such that after about 3 months at about 25° C., about 60% r.H. in a closed vial the pharmaceutical composition contain no more than about 0.1% to about 0.6% of Active Metabolite of Formula II. More preferably, such pharmaceutical composition contains no more than about 0.16%, about 0.50%, or about 0.58% of Active Metabolite of Formula II when stored under such conditions.

Other, exemplary, non-exhaustive examples of such compositions are as follows.

A pharmaceutical composition comprising Fesoterodine and a stabilizer, preferably xylitol, wherein the Fesoterodine in the pharmaceutical composition is stable against degradation at about 25° C., about 60% r.H. in a closed vial such that after about 6 months at about 25° C., about 60% r.H. in a closed vial the pharmaceutical composition contains no more than about 0.2% to about 0.6% of Active Metabolite of Formula II. More preferably, such pharmaceutical composition contains no more than about 0.21%, about 0.53%, or about 0.69% of Active Metabolite of Formula II when stored under such conditions.

A pharmaceutical composition comprising Fesoterodine and a stabilizer, preferably xylitol, wherein the Fesoterodine in the pharmaceutical composition is stable against degradation at about 25° C., about 60% r.H. in a closed vial such that after about 9 months at about 25° C., about 60% r.H. in a closed vial the pharmaceutical composition contains no more than about 0.3% to about 0.7% of Active Metabolite of Formula II. More preferably, such pharmaceutical composition contains no more than about 0.31%, about 0.65%, or about 0.71% of Active Metabolite of Formula II when stored under such conditions.

A pharmaceutical composition comprising Fesoterodine and a stabilizer, preferably xylitol, wherein the Fesoterodine in the pharmaceutical composition is stable against degradation at about 25° C., about 60% r.H. in a closed vial such that after about 12 months at about 25° C., about 60% r.H. in a closed vial the pharmaceutical compositions contain no more than about 0.4% to about 0.9% of Active Metabolite of Formula II. More preferably, such pharmaceutical compositions contain no more than about 0.39%, about 0.75%, or about 0.88% of Active Metabolite of Formula II when stored under such conditions.

A pharmaceutical composition comprising Fesoterodine and a stabilizer, preferably xylitol, wherein the Fesoterodine in the pharmaceutical composition is stable against degradation at about 25° C., about 60% r.H. in a closed vial such that after about 18 months at about 25° C., about 60% r.H. in a closed vial the pharmaceutical composition contains no more than about 0.3% to about 1% of Active Metabolite of Formula II. More preferably, such pharmaceutical composition contains no more than about 0.37%, about 0.85%, or about 1.018% of Active Metabolite of Formula II when stored under such conditions.

A pharmaceutical composition comprising Fesoterodine and a stabilizer, preferably xylitol, wherein the Fesoterodine in the pharmaceutical composition is stable against degradation at about 25° C., about 60% r.H. in a closed vial such that after about 24 months at about 25° C., about 60% r.H. in a closed vial the pharmaceutical compositions contain no more than about 0.8% to about 1.1% of Active Metabolite of Formula II. More preferably, such pharmaceutical composition contains no more than about 0.78%, about 0.94%, or about 1.14% of Active Metabolite of Formula II when stored under such conditions.

A pharmaceutical composition comprising Fesoterodine and a stabilizer, preferably xylitol, wherein the Fesoterodine in the pharmaceutical composition is stable against degradation at about 25° C., about 60% r.H. in a closed vial such that after about 3 months at about 25° C., about 60% r.H. in a closed vial the pharmaceutical composition contains no more than about 1% of total degradation products of Fesoterodine. More preferably, such pharmaceutical composition contains no more than about 1.05% of total hydrolyzation and degradation products of Fesoterodine when stored under such conditions.

A pharmaceutical composition comprising Fesoterodine and a stabilizer, preferably xylitol, wherein the Fesoterodine in the pharmaceutical composition is stable against degradation at about 25° C., about 60% r.H. in a closed vial such that after about 6 months at about 25° C., about 60% r.H. in a closed vial the pharmaceutical composition contains no more than about 1.1% of total hydrolyzation and degradation products of Fesoterodine.

A pharmaceutical composition comprising Fesoterodine and a stabilizer, preferably xylitol, wherein the Fesoterodine in the pharmaceutical composition is stable against degradation at about 25° C., about 60% r.H. in a closed vial such that after about 9 months at about 25° C., about 60% r.H. in a closed vial the pharmaceutical composition contains no more than about 1.2% of total hydrolyzation and degradation products of Fesoterodine.

A pharmaceutical composition comprising Fesoterodine and a stabilizer, preferably xylitol, wherein the Fesoterodine in the pharmaceutical composition is stable against degradation at about 25° C., about 60% r.H. in a closed vial such that after about 12 months at about 25° C., about 60% r.H. in a closed vial the pharmaceutical composition contains no more than about 1.4% of total degradation products of Fesoterodine. More preferably, such pharmaceutical compositions contain no more than about 1.37% of total hydrolyzation and degradation products of Fesoterodine when stored under such conditions.

A pharmaceutical compositions comprising Fesoterodine and a stabilizer, preferably xylitol, wherein the Fesoterodine in the pharmaceutical composition is stable against degradation at about 25° C., about 60% r.H. in a closed vial such that after about 18 months at about 25° C., about 60% r.H. in a closed vial the pharmaceutical composition contains no more than about 1.3% of total degradation products of Fesoterodine. More preferably, such pharmaceutical composition contains no more than about 1.26% of total hydrolyzation and degradation products of Fesoterodine when stored under such conditions.

A pharmaceutical composition comprising Fesoterodine and a stabilizer, preferably xylitol, wherein the Fesoterodine in the pharmaceutical composition which is stable against degradation at about 25° C., about 60% r.H. in a closed vial such that after about 24 months at about 25° C., about 60% r.H. in a closed vial the pharmaceutical composition contains no more than about 2% of total degradation products of Fesoterodine. More preferably, such pharmaceutical composition contains no more than about 1.95% of total hydrolyzation and degradation products of Fesoterodine when stored under such conditions.

In another embodiment, the production of the pharmaceutical composition for the oral administration of Fesoterodine or a pharmaceutically acceptable salt thereof comprises granulating Fesoterodine with a stabilizer selected from the group consisting of sorbitol, xylitol, polydextrose, isomalt, dextrose, and combinations thereof, preferably a sugar alcohol like xylitol or sorbitol.

Thus, the production of granulates comprising granulating a mixture of Fesoterodine or a salt thereof, with a suitable excipient such as a stabilizer selected from the group consisting of sorbitol, xylitol, polydextrose, isomalt, dextrose, and combinations thereof, preferably a sugar alcohol, preferably sorbitol or xylitol, and more preferably xylitol, forms a further aspect of the disclosure herein.

Further provided are granulates of Fesoterodine formed by such a process with a suitable excipient, such as a stabilizer selected from the group consisting of sorbitol, xylitol, polydextrose, isomalt, dextrose, and combinations thereof, preferably a sugar alcohol, preferably sorbitol or xylitol, and more preferably xylitol.

Granulate produced from such a granulation step preferably has a Fesoterodine/stabilizer ratio of about 1-30% [w/w], more preferably about 1-20% [w/w], more preferably about 3-15% [w/w], and even more preferable about 5-10% [w/w]. In a particularly preferred embodiment, granulate includes a Fesoterodine/xylitol or Fesoterodine/sorbitol ratio of about 1-30% [w/w], preferably about 1-20% [w/w], more preferably about 3-15% [w/w], and even more preferably about 5-10% [w/w].

The average size of the granulate can be controlled by usual techniques such as sieving or milling, and typically may be below about 4 mm, preferably below about 2 mm, more preferably below about 1 mm, and even more preferably below about 0.75 mm, e.g. about 0.5 mm.

Fesoterodine granulates as described herein, particularly if produced in a wet granulation process, are surprisingly stable under humid stress conditions. The granulates can be further processed and incorporated into pharmaceutical compositions that are also surprisingly stable.

It has been further surprisingly found that granulating Fesoterodine with either xylitol or sorbitol provides for enhanced stability during the granulation process as compared to granulating Fesoterodine with either mannitol or maltitol. When Fesoterodine was granulated separately with these four sugar alcohols and tested for the amount of hydrolyzation or total degradation that occurred during granulation, it was found that granulating with xylitol or sorbitol resulted in less degradation products than granulating with mannitol or maltitol. Granulating with xylitol or sorbitol led to the formation of about 0.06% to about 0.07% of hydrolyzation products and total degradation products, while granulating with mannitol or maltitol led to the formation of about 0.42% to about 0.73% of hydrolyzation products and total degradation products. (See Table 6).

The surprisingly superior results observed for granulation with xylitol or sorbitol were also observed when Fesoterodine granulates including xylitol or sorbitol were used to prepare pharmaceutical compositions. Pharmaceutical compositions in tablet form that were prepared with granulates of Fesoterodine that included xylitol or sorbitol exhibited far less hydrolyzation products and total degradation products (about 0.06% to about 0.11%) than tablets prepared with Fesoterodine granulates containing mannitol or maltitol (about 1.1% to about 1.7%). (See Table 7).

The difference between sorbitol and mannitol is especially surprising since these two sugar alcohols are isomers.

Accordingly, in another embodiment, provided is the use of granulates comprising Fesoterodine and a stabilizer, such as sugar alcohol described herein, for the treatment of urinary incontinence, specifically urinary urge incontinence, urinary urgency and/or urinary frequency and the preparation of a medicament for treating such conditions. Preferably, the granulates which are used for preparing the medicament (such as, e.g., a tablet) comprise a sugar alcohol (such as, e.g., xylitol or sorbitol). The medicament may be in the form of, e.g., a granulate, a capsule, a lozenge, a tablet or a coated tablet, or other solid administration form.

In yet a further embodiment, provided is a pharmaceutical composition for the oral administration of Fesoterodine or a pharmaceutically acceptable salt or solvate thereof, preferably Fesoterodine hydrogen fumarate, that can be obtained by combining or mixing the granulate described herein with at least one further excipient, preferably with at least one type of sustained release agent, such as hydroxypropyl methylcellulose, and optionally other excipients.

In another aspect, the active ingredient (Fesoterodine or a pharmaceutically acceptable salt thereof) and a stabilizer are embedded in a gel matrix formed by at least one type of hydroxypropyl methylcellulose. More preferably, a granulate comprising the active ingredient (Fesoterodine or a pharmaceutically acceptable salt thereof) and a stabilizer, preferably a sugar alcohol selected from xylitol and sorbitol, are embedded in a gel matrix formed by at least one type of hydroxypropyl methylcellulose. Such a formulation comprising Fesoterodine, a stabilizer and a gel matrix formed by at least one type of hydroxypropyl methylcellulose is preferably designed to release Fesoterodine over an extended period of time, preferably to allow for once-daily oral administration. Suitably, such a once-daily formulation contains at least about 20% hydroxypropyl methylcellulose by weight of the total weight of the formulation, and more preferably at least about 25% (w/w), such as between 25% and 65%, and even more preferably at least about 30% (w/w), such as between 30% and 65%, and particularly preferably at least about 35% (w/w) such as between 35% and 55% HPMC.

It has been determined that the presently disclosed formulations that are suitable for once-daily administration in humans exhibit a particular Fesoterodine release profile in in vitro dissolution assays. These formulations and their dissolution profiles form another embodiment of the present disclosure.

The particularly preferred formulations of the present disclosure, such as for examples the formulations "A", "B", "C", "D", "E", "F", "G" and "H" given in Tables 1 and 2 of the Experimental part of this application, were shown in clinical studies and/or in bioequivalence studies to be effective for the once-daily administration in man. They all exhibit a particular Fesoterodine release profile in in-vitro dissolution assays. These formulations and other formulations showing the respective dissolution profiles form another embodiment of the present disclosure.

Pharmaceutical compositions comprising Fesoterodine that show a cumulative Fesoterodine release (in weight percent based on the theoretical amount of Fesoterodine in the formulation) in an in vitro dissolution assay according to USP 711 (in phosphate buffer, about pH 6.8, about 37° C., at about 75 rpm) are disclosed as follows:

(a) about 5 to about 30%, preferably about 6 to about 26% Fesoterodine release after about 1 hour, (b) about 15% to about 40%, preferably about 18% to about 38% Fesoterodine release after about 2 hours, (c) about 35% to about 65%, preferably about 36% to about 56% Fesoterodine release after about 4 hours, and (d) at least about 75%, preferably at least about 80% Fesoterodine release after about 16 hours.

The gel matrix may optionally contain further ingredients. In particular, a filler such as lactose and/or microcrystalline cellulose also may be embedded in the matrix.

In another embodiment, a solid Fesoterodine composition comprises at least two types of hydroxypropyl methylcellulose (HPMC). The two types of hydroxypropyl methylcellulose (HPMC) may be chemically identical but differ in their viscosity, when dissolved in water under standard conditions. Alternatively, two types of HPMC which differ chemically may be used.

A particularly advantageous composition can be obtained when one type of hydroxypropyl methylcellulose has a nominal viscosity of about 100,000 mPa·s (i.e., 100,000±20,000 mPa·s), and the other has a nominal viscosity of about 4,000 mPa·s (i.e., 4,000±1000 mPa·s) when dissolved in water at about 22° C. in a concentration of about 2% by weight.

In one preferred embodiment, the ratio of Fesoterodine or the pharmaceutically active salt or solvate thereof and hydroxypropyl methylcellulose is between about 1:80 and about 1:5 [w/w]. Even more preferred are weight ratios of between about 1:70 and about 1:10 [w/w] and even more preferably between about 1:40 and about 1:15 [w/w].

Another preferred embodiment is a solid pharmaceutical composition that comprises about 0.25 to about 10% [w/w] Fesoterodine or its pharmaceutically acceptable salt or solvate. Most preferred compositions include Fesoterodine in an amount between about 0.5 and about 4% [w/w]. A preferred composition further may contain one or more additional excipient(s), such as one or more filler(s), binder(s) and/or lubricant(s), and among them lactose, microcrystalline cellulose, talc and glycerol dibehenate are particularly preferred.

The pharmaceutical composition provided herein is preferably a granulate, a tablet or a coated tablet.

Components of the Pharmaceutical Composition

A solid pharmaceutical composition, like those that described herein, may comprise the active ingredient Fesoterodine or a pharmaceutically acceptable salt or solvate thereof, at least one type of hydroxypropyl methylcellulose, and optionally other excipients. In a preferred embodiment, the pharmaceutical composition further comprises a stabilizer, such as sugar alcohol chosen from xylitol and sorbitol, particularly xylitol, as one of the excipients.

The compositions are preferably formulated in a unit dosage form. Each unit dosage form can contain from about 0.5 to about 20 mg, preferably about 1-8 mg, and more preferably about 2, about 4, or about 8 mg of Fesoterodine or a pharmaceutically acceptable salt thereof, such as, e.g., the hydrogen fumarate salt. The term "unit dosage form" refers to physically discrete units suitable as unitary dosages for human beings or other mammals, each unit containing a predetermined quantity of Fesoterodine or its salt calculated to produce the desired therapeutic effect, in addition with suitable pharmaceutical excipients. Most preferred are solid administration forms (such as tablets, coated tablets, granulates and capsules) that only require a once-daily administration to the patient to achieve the desired therapeutic effect.

Pharmaceutical excipients that may be present in the compositions described herein include sustained release ("SR") agents, disintegrants, fillers and lubricants. Other excipients can also be included.

Sustained Release ("SR") Agents

The hydroxypropyl methylcellulose (HPMC) or mixture of HPMCs that is a component of the pharmaceutical composition may act as a binder and sustained release agent. It is preferably present in an amount that allows for the formation of a gel matrix from which the active ingredient is gradually released.

In addition, the pharmaceutical composition may comprise further sustained release agents, preferably those that swell upon contact with water such as polyvinylpyrrolidone, hydroxyethylcellulose, hydroxypropylcellulose, other cellulose ethers and esters like methylcellulose, methylethylcellulose, hydroxypropylmethylcellulose, carboxymethylcellulose, starch, pregelatinized starch, polymethacrylate, polyvinylacetate, microcrystalline cellulose, dextrans or mixtures thereof.

In a preferred embodiment, two types of hydroxypropyl methylcellulose of a different viscosity are used. In these mixtures, one HPMC may have a high viscosity and one HPMC may have a low viscosity.

"High viscosity HPMCs" are those having at (22° C.) a nominal viscosity (by Ubbelohde viscometers) of between about 70,000 and about 150,000, and preferably of about 100,000 (i.e., 100,000±20,000) mPa·s when dissolved (about 2% by weight) in water. "Low viscosity HPMCs" refers to HPMCs having at room temperature a nominal viscosity of between about 3,000 and about 20,000, and preferably of about 4,000 mPa·s (i.e., 4,000±1,000 mPa·s) when dissolved (about 2% by weight) in water. Preferably the rate of substitution with methoxyl groups of the HPMCs used is between about 15 und about 35%, and particular preferred between about 18 and about 30%, while the rate of substitution with hydroxypropoxy groups is preferably between about 5 and about 14%, and more preferably between about 7 and about 12%. Suitable qualities are found in, for example, METHOCEL® E4M, METHOCEL® K4M, METHOCEL® K15M and METHOCEL® K100M which are obtainable from the Dow Chemical Company.

Particularly preferred brands are METHOCEL® K100M having a nominal viscosity of about 100,000 mPa·s and METHOCEL® K4M having a nominal viscosity of about 4,000 mPa·s. The weight ratios of METHOCEL® K100M and K4M used in the compositions and formulations described herein can be in the range of about 20:1 to about 1:2, and are preferably in the range of about 10:1 to about 1:1.5, and are even more preferably in the range of about 7:1 to about 1:1.3.

In one embodiment, one distinct type of hydroxypropyl methylcellulose may be used, such as, e.g., HPMC with a nominal viscosity of between about 50,000 and about 120,000 mPa·s, wherein HPMC with a viscosity of between about 50,000 and about 100,000 mPa·s is preferred.

Disintegrants

Further, the compositions and formulations described herein can also contain disintegrants, such as pregelatinized starch, sodium starch glycolate, microcrystalline cellulose, carboxymethylcellulose sodium (CMC-Na), cross-linked CMC-Na, polacrilin potassium, low-substituted hydroxypropylcellulose or mixtures thereof. The presence of a disintegrant in compositions and formulations described herein is not necessary, but may desirable.

Fillers/Binders

The pharmaceutical compositions described herein can further contain fillers and/or binders such as microcrystalline cellulose, powdered cellulose, lactose (anhydrous or monohydrate), compressible sugar, starch (e.g., corn starch or potato starch), pregelatinized starch, fructose, sucrose, dextrose, dextrans, other sugars such as mannitol, maltitol, sorbitol, lactitol and saccharose, siliconized microcrystalline cellulose, calcium hydrogen phosphate, calcium hydrogen phosphate dihydrate, dicalciumphosphate dihydrate, tricalciumphophate, calcium lactate or mixtures thereof.

Preferably, the excipients include at least one filler selected from microcrystalline cellulose and lactose, such as lactose monohydrate. One preferred embodiment includes as filler a combination of microcrystalline cellulose and lactose, wherein the microcrystalline cellulose:lactose ratio can be about 1:1 to about 1:3 [w/w]. A particularly preferred excipient is MICROCELAC® 100, which is a co-processed mixture of about 75% by weight lactose monohydrate and about 25% by weight microcrystalline cellulose, both of pharmacopoeial quality, manufactured by combined spray-drying. In MICROCELAC® 100, both the filling properties of lactose and the binding capacity of microcrystalline cellulose are synergistically co-processed to one excipient providing improved flow properties and better tableting performance to the composition.

The compositions described herein also can comprise binders, such as cellulose derivatives (e.g., methylcellulose and sodium carboxymethylcellulose), gelatin, glucose, lactose, sucrose, polyethylene glycol, polymethacrylates, hydroxypropylcellulose, sugar alcohols (such as, e.g., sorbitol or xylitol), pregelatinized starch and sodium alginate, wherein xylitol and sorbitol are preferred, and wherein xylitol is particularly preferred. These may be helpful to form granules.

If binders are used to form granulates, they preferably can be used in mean particle size of about 1-300 μm, preferably about 1-200 μm, and even more preferably about 5-100 μm. Most preferably, the binder particles should be smaller than about 1 mm.

For example, if xylitol is used to form granules, suitable qualities are provided by XYLITAB® 300 or XYLITOL® CM50 (both produced by Xyrofin Oy, Kotka, Finland and commercialized by Danisco) and XYLITOL 90 (produced by Roquette GmbH, Germany)

Lubricants

The compositions and formulations disclosed herein also can comprise lubricants, antiadherents and/or glidants such as stearic acid, magnesium stearate, calcium stearate, sodium lauryl sulphate, hydrogenated vegetable oil, hydrogenated castor oil, sodium stearyl fumarate, macrogols, glycerol dibehenate, talc, corn starch, silicone dioxide or mixtures thereof.

The preferred lubricants are talc and glycerol dibehenate.

The term "glycerol dibehenate" as used herein shall be considered synonymous with "glyceryl behenate".

Coatings

Optionally, compositions and formulations described herein, including cores/tablets, can be coated with conventional materials used for film coating, e.g., as described in Pharmaceutical Coating Technology, 1995, edited by Graham Cole. Film coating compositions usually contain the following components: polymer(s), plasticizer(s), colorant(s)/opacifier(s), vehicle(s). Minor quantities of flavours, surfactants and waxes also can be used in the film coating solution or suspension. The majority of the polymers used in film coatings are either cellulose derivatives, such as the cellulose ethers, or acrylic polymers and copolymers. Occasionally encountered are high molecular weight polyethylene glycols, polyvinylpyrrolidone, polyvinyl alcohol and waxy materials.

Typical cellulose ethers are hydroxyethylcellulose, hydroxypropylcellulose, hydroxypropyl methylcellulose and methylcellulose. Acrylic polymers comprise a group of synthetic polymers with diverse functionalities. Some of them can be further modified to enhance swelling and permeability by the incorporation of materials such as water soluble cellulose ethers and starches in order to ensure complete disintegration/dissolution of the film.

The commonly used plasticizers can be categorized into three groups: polyols (glycerol, propylene glycol, macrogols), organic esters (phthalate esters, dibutyl sebacetate, citrate esters, triacetin), oils/glycerides (castor oil, acetylated monoglycerides, fractionated coconut oil).

Colorants/opacifiers are classified into several groups: organic dyes and their lakes, inorganic colors, natural colors. Different materials from each group can also be combined in defined ratios.

One suitable composition of a coating suspension (calculated on dry material) comprises:

(a) about 1-99% by weight of polymer, preferably about 1-95% of polymer,
(b) about 1-50% by weight of plasticizer, preferably about 1-40% of plasticizer,
(c) about 0.1-20% of colorant/opacifier, preferably about 0.1-10% of colorant/opacifier.

Film coats may be prepared from ready-to-make preparations which are available on the market. One preferred film-coat material is OPADRY®, particularly OPADRY®blue, which is a mixture of 6 components, i.e., polyvinyl alcohol (film forming agent), PEG (plasticizer), lecithin (emollient), talc (lubricant), titanium dioxide (white pigment), indigo carmine aluminium lake (dye). Depending on the desired opacity, the preferred amount the coating is about 4-6% w/w of the tablet, preferably about 4.5%.

A film coating dispersion or suspension can be prepared by using different solvents (water, alcohols, ketones, esters, chlorinated hydrocarbons), but water is preferred.

Preferred Quantities of Ingredients

Preferred exemplary, non-exhaustive examples of solid pharmaceutical compositions will now be described. All percentages are weight based [w/w], relating to the total weight of the composition, unless indicated otherwise.

In one embodiment is a pharmaceutical composition that comprises:

(a) About 0.5-4.0% [w/w] of Fesoterodine or a salt thereof, preferably Fesoterodine hydrogen fumarate.
(b) About 5-25% [w/w] of a stabilizer, preferably sorbitol or xylitol. The stabilizer preferably has a mean particle size of about 0.001-0.30 mm.
(c) About 20-40% [w/w] of fillers and/or binders, such as lactose monohydrate and microcrystalline cellulose.
(d) About 20-80% [w/w] hydroxypropyl methylcellulose, and preferably about 25-65%, more preferably about 30-65%, and even more preferably about 35-55% [w/w] hydroxypropyl methylcellulose.
(e) About 1-10% [w/w] lubricants, such as glycerol dibehenate and/or talc.

More preferably is a pharmaceutical composition that comprises:

(a) about 0.3-5.0% [w/w] of Fesoterodine or a salt thereof, preferably Fesoterodine hydrogen fumarate;
(b) about 5-25% [w/w] of a stabilizer, preferably sorbitol or xylitol (preferably having a mean particle size of about 0.001-0.30 mm);

(c) about 20-40% [w/w] of a mixture comprising about 45-80%, preferably about 75% [w/w] lactose monohydrate and about 20-55%, preferably about 25% [w/w] microcrystalline cellulose;

(d) about 20-80%, preferably about 25-65%, more preferably about 30-65%, and even more preferably about 35-55% [w/w] hydroxypropyl methylcellulose;

(e) about 1-10% [w/w] lubricants, such as glycerol dibehenate and/or talc.

In another specific embodiment, a pharmaceutical composition comprises (a) about 0.5-4.0% [w/w] of Fesoterodine hydrogen fumarate;

(b) about 5-25% [w/w] of a stabilizer, preferably sorbitol or xylitol (preferably having a mean particle size of about 0.001-0.30 mm);

(c) about 20-40% [w/w] of a mixture comprising about 75% (w/w) lactose monohydrate and about 25% [w/w] microcrystalline cellulose;

(d) about 15-55%, and preferably about 15-40% [w/w] high viscosity hydroxypropyl methylcellulose;

(e) about 5-30%, and preferably about 5-25% [w/w] low viscosity hydroxypropyl methylcellulose;

(f) about 1-5% [w/w] glycerol dibehenate; and (g) about 1-5% [w/w] talc.

A coating may optionally be applied to such a composition. One preferred material for film-coating is OPADRY®, but other coatings are known.

In yet another embodiment is a pharmaceutical composition that comprises:

(a) about 0.1-10%, preferably about 0.2-7%, more preferably between 0.3 and 5%, and even more preferably about 0.5-4.0% Fesoterodine or a salt thereof, preferably the hydrogen fumarate salt, (b) about 20-80%, preferably about 25-65%, more preferably about 30-65%, and even more preferably about 35-55% HPMC, wherein the HPMC may comprise two or more different types, such as a high-viscosity HPMC (e.g., METHOCEL® K100M) and a low-viscosity HPMC (e.g., METHOCEL® K4M). The ratio of high-viscosity HPMC to low-viscosity HPMC may be about 20:1 to about 1:2 [w/w], and preferably is about 10:1 to about 1:1.5 [w/w], and even more preferably is about 7:1 to about 1:1.3 [w/w].

(c) about 1-45%, preferably about 2-35%, and more preferably about 5-25% xylitol or sorbitol, (d) about 10-70%, preferably about 15-50%, and more preferably about 20-40% a filler, and (e) about 0.5-10%, preferably about 1-8%, and more preferably about 2-7% a lubricant.

A particularly preferred solid pharmaceutical composition comprises [w/w]:

| | |
|---|---|
| Fesoterodine hydrogen fumarate | about 0.5-4.0% |
| Xylitol | about 5-25% |
| MICROCELAC ® 100 | about 20-40% |
| HPMC (high viscosity) | about 15-40% |
| HPMC (low viscosity) | about 5-25% |
| Glycerol dibehenate | about 1-5% |
| Talc | about 1-5% | and optionally a pharmaceutically acceptable coating. In this particularly preferred embodiment the preferred mean particle size of xylitol is about 1-300 μm, more preferably about 1-200 μm, and even more preferably about 5-100 μm. In the most preferred embodiment, all particles should preferably be less than about 1 mm.

Another preferred embodiment is a coated tablet comprising a core that further comprises:

| | |
|---|---|
| Fesoterodine hydrogen fumarate | about 4.0 mg |
| Xylitol (preferably with a mean particle size of about 0.001-0.30 mm) | about 36.0 mg |
| MICROCELAC ® 100 | about 121.5 mg |
| HPMC having a nominal viscosity of about 100,000 mPa · s when dissolved (about 2% by weight) in water, preferably METHOCEL ® K100M | about 70.0 mg |
| HPMC having a nominal viscosity of about 4,000 mPa · s when dissolved (about 2% by weight) in water, preferably METHOCEL ® K4M | about 70.0 mg |
| Glycerol dibehenate | about 10.0 mg |
| Talc | about 8.5 mg | and a coating, preferably OPADRY®, and more preferably about 15 mg OPADRY®.

The pharmaceutical compositions in addition may contain minor amounts (less than about 3%, and more preferably less than about 1% by weight) of impurities. Moreover, the compositions preferably contain no more than about 5% by weight water which may be used during the manufacturing process.

In yet another embodiment is a coated tablet comprising a core comprising:

| | |
|---|---|
| Fesoterodine hydrogen fumarate | about 8.0 mg |
| Xylitol (preferably with a mean particle size of about 0.001-0.20 mm) | about 72.0 mg |
| MICROCELAC ® 100 | about 77.5 mg |
| HPMC having a nominal viscosity of about 100,000 mPa · s when dissolved (about 2% by weight) in water, preferably METHOCEL ® K100M | about 120.0 mg |
| HPMC having a nominal viscosity of about 4,000 mPa · s when dissolved (about 2% by weight) in water, preferably METHOCEL ® K4M | about 24.0 mg |
| Glycerol dibehenate | about 10.0 mg |
| Talc | about 8.5 mg | and a coating, preferably OPADRY®, and more preferably about 15 mg of OPADRY®.

Preparation Process

The present pharmaceutical compositions can be prepared by known procedures, e.g., compression or granulation. In the preparation of the pharmaceutical compositions, Fesoterodine or a pharmaceutically acceptable salt or solvate thereof usually can be mixed with an excipient or mixture of excipients, or diluted by an excipient or mixture of excipients, or enclosed within an excipient or mixture of excipients.

Granulates comprising Fesoterodine or a pharmaceutically acceptable salt or solvate thereof can be produced by granulation, for example by dry granulation or, preferably, by wet granulation. Wet granulation is usually performed by adding a liquid, e.g., water, to a mixture of the active ingredient (i.e., Fesoterodine or its salts or solvates) and the binder used to form granulates (e.g., a sugar alcohol selected from sorbitol and xylitol) and then granulating the wet mixture.

In one embodiment, wetting a mixture of Fesoterodine and sorbitol or xylitol can be performed in conventional granulation equipment, such as a high shear mixer (e.g., Lödige MGT 250) or fluid bed spray dryer (e.g., Glatt GPCG 60/90), by spraying a liquid such as, e.g., ethanol, isopropanol, aqueous solutions of ethanol or isopropanol, or preferably water or an aqueous granulating liquid onto the mixture of Fesoterodine and xylitol or sorbitol by conventional pharmaceutical techniques. Wetting also can be performed by direct addition of a liquid, such as water or an aqueous granulating liquid to the above mixture during a mixing operation in a proper mixing device, e.g., a high-shear mixer granulator. The term "aqueous granulating liquid" refers to an aqueous dispersion which contains purified or demineralised water (Ph.Eur.) as a liquid and a solid substance which is dispersed, suspended or dissolved in the liquid.

The mixing of excipients alone or with Fesoterodine may be effected in conventional devices used for mixing of powders, e.g., motionless (passive) mixers, fluidized bed, diffusion, biconic diffusion, biconic, turbular, cubic, planetary, Y—, V-shaped or high-shear mixers.

For drying the wet granulate, conventional drying systems such as fluid-bed dryers or drying chambers can be used.

In the processes as described above, compression, in particular to tablets, can be effected using an automatic rotary tablet machine from different manufacturers of equipment for use in the pharmaceutical industry.

Conventional equipment can be used for applying a film coating, such as the Driacoater 1200 coating system or other conventional coating pans used in the pharmaceutical industry.

The process for preparing the pharmaceutical composition can be carried out as a wet or dry granulation process or as a direct compression process.

It has been determined, surprisingly, that Fesoterodine is particularly stable in a pharmaceutical composition that is produced in the presence of a liquid, preferably water, and particularly if the pharmaceutical composition comprising Fesoterodine is produced via a wet granulation process, particularly preferably if water is used as the liquid in the wet granulation process.

Since Fesoterodine contains an ester functional group, it was expected that exposing Fesoterodine to water would lead to more hydrolyzation of the ester than not exposing Fesoterodine to water. Thus, prior to the Applicants' work, more hydrolyzation was expected from wet granulation processes than from dry granulation processes. Instead, surprisingly, for example, pharmaceutical compositions of Fesoterodine and xylitol in the form of tablets that were produced by a process including wet granulation were tested for stability for 6 weeks at 40° C., 75% r.H. in closed vials and were found to contain only about 0.5% hydrolyzation product (i.e., Active Metabolite) and only about 0.7% total degradation products (see Table 8). In contrast, tablets comprising Fesoterodine and xylitol that were produced by direct compression (i.e., a process not including wet granulation), stored under the same conditions, were found to contain about 1.3% hydrolyzation product (i.e., Active Metabolite) and about 2.1% total degradation products (see Table 8).

Accordingly, another embodiment provide is a pharmaceutical composition comprising Fesoterodine and xylitol, which pharmaceutical composition contains no more than about 0.5% (and in particular, no more than about 0.48%) hydrolyzation product (i.e., Active Metabolite) and no more than about 0.7% (and in particular, no more than about 0.68%) total degradation products after storage for 6 weeks at about 40° C., about 75% r.H. in closed vials.

Pharmaceutical compositions of Fesoterodine and xylitol in the form of tablets that were produced by a process including wet granulation were tested for stability for 6 months at room temperature in closed vials, and were found to contain only about 0.2% hydrolyzation product (i.e., Active Metabolite) (by weight as compared to Fesoterodine) and only about 1.3% total degradation products (see Table 9). In contrast, tablets comprising Fesoterodine and xylitol that were produced by dry granulation, stored under the same conditions, were found to contain about 0.8% hydrolyzation product (i.e., Active Metabolite) and about 1.7% total degradation products (by weight as compared to Fesoterodine) (see Table 9).

Accordingly, also provided herein is a pharmaceutical composition comprising Fesoterodine and xylitol, which pharmaceutical composition contains no more than about 0.2% (and in particular, no more than about 0.27%) hydrolyzation product (i.e., Active Metabolite) and no more than about 1.3% (and in particular, no more than about 1.33%) total degradation products after storage for 6 months at room temperature in closed vials.

Also provided is an improved process for producing a granulate of Fesoterodine and a stabilizer, preferably xylitol or sorbitol comprising the step of wet granulating Fesoterodine and the stabilizer. Similarly, provided is a granulate of Fesoterodine and a stabilizer, preferably xylitol or sorbitol produced by a process comprising the step of wet granulating Fesoterodine and the stabilizer, preferably xylitol or sorbitol, particularly preferably xylitol. In a preferred embodiment, water is used in wet granulation.

The process of wet granulation may comprise:
  (a) providing a mixture of Fesoterodine and a stabilizer, such as a stabilizing sugar alcohol, including a sugar alcohol selected from xylitol or sorbitol;
  (b) adding water to the mixture to form a wet mixture; and
  (c) granulating the wet mixture.

The ratio of Fesoterodine:stabilizer in the mixture of step (a) may be from about 1:1 to about 1:20, and is more preferably from about 1:1 to about 1:10.

In a preferred embodiment, the wet aqueous granulation process comprises:
  (a) providing Fesoterodine that is optionally micronized or a pharmaceutically acceptable salt or solvate thereof,
  (b) granulating the Fesoterodine or the salt or solvate thereof together with suitable excipients such as, e.g., a stabilizer such as a sugar alcohol selected from sorbitol or xylitol, using water or a water-based dispersion as granulation liquid to obtain a granulate,
  (c) mixing the above, optionally with HPMC and/or other excipients to give a compression mixture,
  (d) compressing the compression mixture to the desired form, and
  (e) optionally applying a coating.

In yet another embodiment, a pharmaceutical composition comprising Fesoterodine or pharmaceutically acceptable salts thereof is produced by:
  (a) providing a dry mixture of Fesoterodine and a sugar alcohol selected from xylitol and sorbitol;
  (b) adding a liquid, preferably water, to the mixture obtained in (a) to form a wet mixture;
  (c) granulating the wet mixture;
  (d) drying the granulates;
  (e) mixing the granulates with at least one type of hydroxypropyl methylcellulose to form a mixture of granulates and hydroxypropyl methylcellulose and optionally adding other excipients;
  (f) pressing the mixture of granulates and hydroxypropyl methylcellulose into tablets; and
  (g) coating the tablets.

The pharmaceutical compositions described herein in the form of a tablet, or optionally a coated tablet, are surprisingly stable under harsh conditions (40° C., 75% relative humidity). The shelf-life of a preferred composition at room temperature can be as long as 2 years.

EXAMPLES

1. Preparation of the Granulate by Wet Granulation 6.4 kg of Fesoterodine fumarate and 57.6 kg of xylitol were weighed separately. If xylitol had agglomerated, it was passed through a sieve (1.5 mm). Fesoterodine fumarate and xylitol were passed through a sieve (0.8 mm). The materials were transferred into a suitable high-shear mixer granulator (e.g., Lödige Diosna V25 or Lödige Diosna P1/6) and mixed for 1 minute. 3.6 L of purified water were added to the dry mixture while stirring. The mixture was stirred with a chopper for 90 to 120 seconds. The mixer was emptied, and the contents were transferred to a sieving machine. The wet granulate was passed through a sieve or a screen (4.0 mm). The sieved granulate was dried on trays at 45° C. for a minimum of 8 h in a drying chamber/oven until a water content of not more than 0.5%. The dried granulate was passed through a sieve (0.5 to 1.0 mm). Mixing (speed: 8 rpm) was performed for 5 minutes.

2. Preparation of the Press Mixture

2.1. 4 mg SR Tablets 16.0 kg of the granulate and 48.6 kg of MICROCELAC® 100 were passed through a sieve (0.5 to 1.0 mm) (e.g., FREWITT), transferred into a mixing container and mixed (speed: 8 rpm) for 10 minutes. 28.0 kg of hypromellose (e.g., METHOCEL® K100M), 28.0 kg of hypromellose (e.g., METHOCEL® K4M), 4.0 kg of glycerol dibehenate and 3.4 kg of talc were added to the pre-mixture and mixed (speed: 8 rpm) for 1 minute. The mixture was passed through a sieve (0.5 to 1.0 mm) (e.g., FREWITT) into a mixing container. Mixing (speed: 8 rpm) for 10 to 30 minutes was performed.

2.2. 8 mg SR Tablets 32.0 kg of the granulate and 31.0 kg of MICROCELAC® 100 were passed through a sieve (0.5 to 1.0 mm) (e.g., FREWITT), transferred into a mixing container and mixed (speed: 8 rpm) for 10 minutes. 48.0 kg of hypromellose (e.g., METHOCEL® K100M), 9.6 kg of hypromellose (e.g., METHOCEL® K4M), 4.0 kg of glycerol dibehenate and 3.4 kg of talc were added to the pre-mixture and mixed (speed: 8 rpm) for 1 minute. The mixture was passed through a sieve (0.5 to 1.0 mm) (e.g., FREWITT) into a mixing container. Mixing (speed: 8 rpm) for 10 to 30 minutes was performed.

3. Tabletting

The finished press mixture was transferred to a rotary tablet machine and compressed to oval biconvex tablets.

4. Coating

OPADRY® and purified water were added to a vessel under stirring. The mixture was stirred for at least 1 h. Then the suspension was passed through a sieve of a suitable size (e.g., 300 μm) and transferred into the solution tank of the coating pan (e.g., Driacoater 1200). A film coating was applied on the cores under constant stirring of the suspension until the weight per coated tablet was 335 mg.

5. Exemplary Compositions of Sustained Release Compositions

TABLE 1

Compositions of Fesoterodine 4 mg SR tablets

| | EXAMPLES | | |
|---|---|---|---|
| | A | B | C |
| Tablet Core | | | |
| Fesoterodine hydrogen fumarate | 4.0 | 4.0 | 4.0 |
| Xylitol | 36.0 | 36.0 | 36.0 |
| Lactose monohydrate (75%)/ microcryst. cellulose (25%) (e.g. MICROCELAC® 100) | 124.5 | 121.5 | 121.5 |
| Hypromellose (e.g. METHOCEL® K100M) | 70.0 | 70.0 | 70.0 |
| Hypromellose (e.g. METHOCEL® K4M) | 70.0 | 70.0 | 70.0 |
| Glycerol dibehenate | 8.0 | 10.0 | 10.0 |
| Talc | 7.5 | 8.5 | 8.5 |
| Purified water | q.s.* | q.s.* | q.s.* |
| Film-coat | White 10.0 | White 10.0 | Blue 15.0 |
| Purified water | q.s.* | q.s.* | q.s.* |
| Total | 330.0 | 330.0 | 335.0 | q.s. = quantum satis, as much as needed
*removed during drying of the wet granulate or during film-coating, to a total residual moisture of approx. 2.5-3.5%
Numbers are in milligrams.

TABLE 2

Compositions of Fesoterodine 8 mg SR tablets

| | EXAMPLES | | | | |
|---|---|---|---|---|---|
| | D | E | F | G | H |
| Tablet core | | | | | |
| Fesoterodine hydrogen fumarate | 8.0 | 8.0 | 8.0 | 8.0 | 8.0 |
| Xylitol | 72.0 | 72.0 | 72.0 | 72.0 | 72.0 |
| Lactose monohydrate (75%)/ microcryst. cellulose (25%) (e.g. MICROCELAC® 100) | 80.5 | 140.0 | 80.5 | 77.5 | 77.5 |
| Hypromellose (e.g. METHOCEL® K100M) | 120.0 | 165.0 | 120.0 | 120.0 | 120.0 |
| Hypromellose (e.g. METHOCEL® K4M) | 24.0 | 33.0 | 24.0 | 24.0 | 24.0 |
| Glycerol dibehenate | 8.0 | 11.0 | 8.0 | 10.0 | 10.0 |
| Talc | 7.5 | 11.0 | 7.5 | 8.5 | 8.5 |
| Purified water | q.s.* | q.s.* | q.s.* | q.s.* | q.s.* |
| Film-coat | 15.0 | 15.0 | 10.0 | 10.0 | 15.0 |
| Purified water | q.s.* | q.s.* | q.s.* | q.s.* | q.s.* |
| Total | 335.0 | 455.0 | 330.0 | 330.0 | 335.0 | q.s. = quantum satis, as much as needed
*removed during drying of the wet granulate or during film-coating, to a total residual moisture of approx. 2.5-3.0%
Numbers are in milligrams.

6. Stability Tests a) Storage of tablets in closed containers

The tablet compositions of Examples A, F, and G containing 4, 8, and 8 mg Fesoterodine hydrogen fumarate, respectively, were tested for stability. The results are shown in Table 3 below.

The purity of the Fesoterodine in the tablets was measured under the following HPLC conditions and taken as an indication of stability:

Column: Prontosil Spheribond CN, 5 μm, 250 mm×4 mm or equivalent

Component A: Water/trifluoroacetic acid 1000/1 (v/v)

Component B: Acetonitrile/trifluoroacetic acid 1000/1 (v/v)

Gradient profile:

| Time (min) | % A | % B |
|---|---|---|
| 0.0 | 75 | 25 |
| 10.0 | 75 | 25 |
| 10.1 | 50 | 50 |
| 19.0 | 50 | 50 |

Flow rate: 1.2 mL/min.

Column temperature: 35° C.

Injection volume: 75 μL

Detection wavelength: 220 nm

The retention time of the Active Metabolite was about 4.7 min; response factor: 1.5.

Evaluation of the HPLC results was by the area percent method.

The average content of hydrolyzation or degradation product (% by weight) observed after storage at 25° C., 60% r.H. in closed containers (25 mL brown glass bottle sealed with a plastic cap and a paraffin sealing, without any desiccant), for representative compositions is shown in Table 3 below.

TABLE 3

| Time of Storage | Ex. A 4 mg % Hydr | Ex. F 8 mg % Hydr | Ex. G 8 mg % Hydr | Ex. G 8 mg % Degr |
|---|---|---|---|---|
| Initial | 0.47 | 0.51 | 0.11 | 0.69 |
| 3 months | 0.50 | 0.58 | 0.16 | 1.05 |
| 6 months | 0.53 | 0.69 | 0.21 | 1.10 |
| 9 months | 0.70 | 0.65 | 0.31 | 1.20 |
| 12 months | 0.88 | 0.75 | 0.39 | 1.37 |
| 18 months | 0.85 | 1.01 | 0.37 | 1.26 |
| 24 months | 0.94 | 1.14 | 0.78 | 1.95 |

% Hydr = Hydrolyzation product of Fesoterodine (Active Metabolite) [% by weight]
% Degr = Total degradation of Fesoterodine [% by weight]

b) Storage in Open Vials

Fesoterodine hydrogen fumarate, a granulate containing Fesoterodine hydrogen fumarate and xylitol in a weight-ratio of 10:90, as well as a composition comprising Fesoterodine hydrogen fumarate and xylitol were stored in open vials (25 ml brown glass bottles) for up to 12 weeks at 40° C. and 75% r.H. The results are shown in Table 4 below.

The degradation of Fesoterodine was measured by HPLC. The following conditions were used to measure degradation products in the stability testing of Fesoterodine hydrogen fumarate:

Column: Polaris C18-Ether, 3 μm, 250 mm×4.6 mm

Eluent A: Water/methanesulfonic acid 1000:0.5 (v/v)

Eluent B: Acetonitrile/methanesulfonic acid 1000:0.5 (v/v)

Typical gradient profile:

| Time (min) | % A | % B |
|---|---|---|
| 0.0 | 67 | 33 |
| 16.0 | 38 | 62 |
| 18.0 | 0 | 100 |

Column temperature: 35° C.

Flow rate: 1.2 mL/min

Detection wavelength: 220 nm

Injection volume: 20 μL

The retention time of the Active Metabolite was about 4.1 min (rrt=0.50); response factor: 1.4.

Evaluation of the HPLC results was by the area percent method.

A comparison of the observed average purity of a Fesoterodine-containing granulate and a corresponding composition as compared to pure Fesoterodine after open storage under stress conditions is set out in Table 4, wherein values are indicated in % of Fesoterodine hydrogen fumarate remaining at various times.

TABLE 4

| Storage at 40° C. and 75% r.H. | Fesoterodine (pure) | Granulate containing Fesoterodine/Xylitol 10%/90% (wt/wt) | Composition (Ex. B) |
|---|---|---|---|
| Initial | 98.96% | 99.04% | 99.18% |
| 1 week | 98.56% | 98.83% | not measured |
| 2 weeks | 97.67% | 98.61% | 96.98% |
| 4 weeks | 94.32% | 97.45% | 94.79% |
| 12 weeks | 50.39% | 92.83% | 89.76% | c) Stability of Blends of Fesoterodine with Sugar Alcohols

Blends of Fesoterodine hydrogen fumarate with xylitol, sorbitol, mannitol and maltitol were stored for 6 weeks and 3 months in closed vials at 25° C. and 60% r.H., in closed vials at 40° C. and 75% r.H., or in open vials at 40° C. and 75% r.H. and then tested for stability by measuring the purity of Fesoterodine. The initial purity of the Fesoterodine in the blends was 99.7%.

Table 5a shows that while Fesoterodine is stabilized against degradation in open vials when mixed with xylitol or sorbitol, it decomposes more rapidly when mixed with mannitol and maltitol.

TABLE 5a

Purity of Fesoterodine in blends after 6 weeks and 3 months

| Blend Fesoterodine with: | closed vial 25° C., 60% r.H. | closed vial 40° C., 75% r.H. | open vial 40° C., 75% r.H. |
|---|---|---|---|
| Xylitol 1:9 | | | |
| 6 weeks | 99.6 | 98.7 | 98.7 |
| 3 months | 99.6 | | 98.2 |
| Xylitol 1:1 | | | |
| 6 weeks | 99.6 | 95.7 | 98.6 |
| 3 months | 99.6 | | 65.2 |

TABLE 5a-continued

Purity of Fesoterodine in blends after 6 weeks and 3 months

| Blend Fesoterodine with: | closed vial 25° C., 60% r.H. | closed vial 40° C., 75% r.H. | open vial 40° C., 75% r.H. |
|---|---|---|---|
| Sorbitol 1:9 | | | |
| 6 weeks | 99.4 | 98.2 | 99.0 |
| 3 months | 99.0 | | 98.5 |
| Sorbitol 1:1 | | | |
| 6 weeks | 99.6 | 99.3 | 98.7 |
| 3 months | 99.5 | | 70.2 |
| Mannitol 1:9 | | | |
| 6 weeks | 99.6 | 89.6 | 91.7 |
| 3 months | 99.4 | | 42.8 |
| Mannitol 1:1 | | | |
| 6 weeks | 99.7 | 94.4 | 94.5 |
| 3 months | 99.6 | | 41.3 |
| Maltitol 1:9 | | | |
| 6 weeks | 99.6 | 94.2 | 95.4 |
| 3 months | 99.5 | | 53.7 |
| Maltitol 1:1 | | | |
| 6 weeks | 99.6 | 95.1 | 96.3 |
| 3 months | 99.6 | | 51.2 |
| Fesoterodine | | | |
| 6 weeks | 99.6 | 99.3 | 96.3 |
| 3 months | 99.7 | | 53.1 |

Table 5b shows that lactose destabilizes Fesoterodine, while xylitol is capable of reducing the destabilizing effect of lactose

TABLE 5b

Purity of Fesoterodine in blends after 6 weeks and 3 months

| Blend Fesoterodine with: | closed vial 25° C., 60% r.H. | closed vial 40° C., 75% r.H. | open vial 40° C., 75% r.H. |
|---|---|---|---|
| Lactose 1:9 | | | |
| 6 weeks | 99.7 | 98.0 | 86.2 |
| 3 months | 99.6 | | 42.8 |
| Lactose 1:1 | | | |
| 6 weeks | 99.6 | 97.3 | 96.2 |
| 3 months | 99.5 | | 59.8 |
| Lactose/Xylitol 1:20:9 | | | |
| 6 weeks | 99.9 | 99.2 | 98.8 |
| 3 months | 99.6 | | 97.8 |
| Lactose/Xylitol 1:1:1 | | | |
| 6 weeks | 99.6 | 97.1 | 98.6 |
| 3 months | 99.5 | | 83.8 |

(d) Degradation of Fesoterodine During Granulate Production

Granulates of Fesoterodine with various sugars, sugar alcohols, polyols, or derivatives thereof were produced as described in Example 1. After production of the granulates, and after six weeks and three months of storage under various conditions, the purity of the Fesoterodine in the granulates was determined. The results are given in Table 6.

TABLE 6

Purity of Fesoterodine in different granulates

| Feso-Granulate with | Closed vial 25° C., 60% r.H | | Closed vial 40° C., 75% r.H | | Open vial 40° C., 75% r.H | |
|---|---|---|---|---|---|---|
| | % Hydr | % Degr | % Hydr | % Degr | % Hydr | % Degr |
| Mannitol 1:9 | | | | | | |
| Start | 0.45 | 0.87 | 0.45 | 0.87 | 0.45 | 0.87 |
| 6 weeks | 6.08 | 8.03 | 10.40 | 18.86 | 28.14 | 40.72 |
| 3 months | 10.37 | 12.83 | 28.15 | 57.64 | 40.52 | 63.62 |
| Maltitol 1:9 | | | | | | |
| Start | 0.42 | 0.83 | 0.42 | 0.83 | 0.42 | 0.83 |
| 6 weeks | 3.80 | 5.43 | 7.90 | 16.77 | 22.14 | 45.52 |
| 3 months | 13.85 | 17.71 | 11.44 | 29.72 | 43.11 | 72.05 |
| Xylitol 1:9 | | | | | | |
| Start | 0.06 | 0.06 | 0.06 | 0.06 | 0.06 | 0.06 |
| 6 weeks | 0.12 | 0.22 | 0.23 | 0.37 | 0.58 | 1.25 |
| 3 months | 0.23 | 0.28 | 7.04 | 14.77 | 1.14 | 4.01 |
| Sorbitol 1:9 | | | | | | |
| Start | 0.07 | 0.07 | 0.07 | 0.07 | 0.07 | 0.07 |
| 6 weeks | 0.36 | 0.51 | 1.47 | 2.79 | 0.48 | 0.91 |
| 3 months | 0.74 | 0.99 | 7.58 | 18.03 | 0.91 | 3.38 |
| Lactose 1:9 | | | | | | |
| Start | 0.35 | 0.63 | 0.35 | 0.63 | 0.35 | 0.63 |
| 6 weeks | nd | nd | 19.67 | 46.23 | 20.69 | 44.73 |
| 3 months | 20.90 | 27.90 | 17.32 | 92.55 | 21.14 | 88.25 |
| Avicel 1:9 | | | | | | |
| Start | 0.19 | 0.55 | 0.19 | 0.55 | 0.19 | 0.55 |
| 6 weeks | nd | nd | 8.47 | 13.31 | 23.57 | 55.14 |
| 3 months | 5.43 | 6.92 | 10.65 | 19.81 | 20.78 | 64.40 |
| Dextrose monohydr 1:9 | | | | | | |
| 3 weeks | 0.36* | 0.83* | 0.73 | 1.3 | nd | nd |
| 6 weeks | 0.39* | 0.81* | 1.3 | 2.3 | | |
| Isomalt 1:9 | | | | | | |
| 3 weeks | 0.39* | 0.79* | 0.75 | 1.3 | nd | nd |
| 6 weeks | 0.73* | 1.2* | 1.0 | 1.8 | | |
| Polydextrose 1:9 | | | | | | |
| 3 weeks | 0.21* | 0.58* | 0.41 | 0.8 | nd | nd |
| 6 weeks | 0.25* | 0.71* | 0.42 | 0.9 | | |

% Hydr = Hydrolyzation product of Fesoterodine (Active Metabolite) [% by weight]
% Degr = Total degradation products of Fesoterodine [% by weight]

(e) Degradation of Fesoterodine During Tablet Production

Granulates of Fesoterodine with various sugars and sugar alcohols were produced as described in Example 1. These granulates were then used to produce 4 mg tablets according to Example 2.1 and with the composition given as "Example C" in Table 1, as well as wherein the xylitol was substituted with mannitol, maltitol, sorbitol, or lactose. After production of the tablets, and after six weeks and three months of storage under various conditions, the amount of degradation of the Fesoterodine was determined by measuring the purity of the Fesoterodine. The results are shown in Table 7.

TABLE 7

Purity of Fesoterodine in tablets with various sugar
and sugar alcohol granulates

| Tablets Fesoter. with: | Closed vial 25° C., 60% r.H 6 weeks | | Closed vial 40° C., 75% r.H 6 weeks | | Open vial 40° C., 75% r.H 6 weeks | |
|---|---|---|---|---|---|---|
| | % Hydr | % Degr | % Hydr | % Degr | % Hydr | % Degr |
| Mannitol 1:9 | | | | | | |
| Start | 1.23 | 1.95 | 1.23 | 1.95 | 1.23 | 1.95 |
| 6 weeks | 6.29 | 8.61 | 14.68 | 29.32 | 22.24 | 42.84 |
| 3 months | 16.58 | 23.21 | 24.06 | 60.11 | 26.62 | 69.83 |
| Maltitol 1:9 | | | | | | |
| Start | 1.11 | 1.78 | 1.11 | 1.78 | 1.11 | 1.78 |
| 6 weeks | 5.31 | 7.68 | 11.46 | 23.67 | 22.38 | 40.38 |
| 3 months | 11.16 | 15.95 | 26.87 | 68.52 | 26.65 | 69.94 |
| Xylitol 1:9 | | | | | | |
| Start | 0.06 | 0.12 | 0.06 | 0.12 | 0.06 | 0.12 |
| 6 weeks | 0.18 | 0.31 | 1.09 | 1.54 | 4.40 | 6.78 |
| 3 months | 0.64 | 0.88 | 3.91 | 6.68 | 6.76 | 13.51 |
| Sorbitol 1:9 | | | | | | |
| Start | 0.11 | 0.21 | 0.11 | 0.21 | 0.11 | 0.21 |
| 6 weeks | 0.39 | 0.64 | 2.14 | 3.66 | 6.72 | 10.48 |
| 3 months | 1.03 | 1.29 | 9.81 | 18.54 | 10.79 | 20.49 |
| Lactose 1:9 | | | | | | |
| Start | 0.67 | 1.03 | 0.67 | 1.03 | 0.67 | 1.03 |
| 6 weeks | 3.94 | 5.47 | 22.96 | 41.54 | 23.56 | 43.39 |
| 3 months | 11.14 | 15.24 | 41.54 | 51.14 | 42.74 | 51.17 |

% Hydr. = Hydrolyzation product of Fesoterodine (Active Metabolite) [% by weight]
% Degr. = Total degradation products of Fesoterodine [% by weight]

(f) Stability of Fesoterodine in Tablets after Wet Granulation vs. Direct Compression Tablets with the composition of "Example C" of Table 1 were obtained either (a) by the process according to Examples 1 and 2.1., i.e., by wet granulating Fesoterodine and xylitol or (b) by the direct compression of all excipients. The tablets were then subjected to stability testing for 6 weeks and 3 months at 40° C., 75% r.H. in closed vials. The results are shown in Table 8.

TABLE 8

Comparison of Fesoterodine 6-week and 3-months-
stress stability in tablets after (a) wet granulation or (b)
direct compression in the presence of xylitol

| Tablets produced by | % Hydrolyzation by weight | % Total Degradation by weight |
|---|---|---|
| wet granulation | | |
| 6 weeks | 0.48 | 0.68 |
| 3 months | 1.69 | 2.92 |
| direct compression | | |
| 6 weeks | 1.32 | 2.08 |
| 3 months | 4.71 | 8.72 |

Hydrolyzation by weight refers to the percent by weight of Active Metabolite.

Total degradation by weight refers to the percent by weight of total degradation products of Fesoterodine.

(g) Stability of Fesoterodine in Tablets after Dry Granulation

Tablets with the composition of "Example C" of Table 1 were prepared as follows:

3.5 kg Fesoterodine hydrogen fumarate was blended with 31.5 kg xylitol and sieved through a 0.032" sieve. The blend was dry compacted with a roller compactor at a pressure of 1250 psi. The compacted ribbons were granulated via a 20 mesh screen in an oscillator granulator. The material was further screened through a 0.040" grater screen. 33.91 MICROCELAC® 100 and 15.09 kg hypromellose K100M were added and blended. After sieving over 0.040", the blend was dry compacted at 700 psi. After compaction, the material was granulated via a 16 mesh oscillating sieve and finally via a 0.062" grater screen. 37.41 kg hypromellose K100 M, 0.5 kg hypromellose K4M and 3.72 kg talc were added, blended and the blend sieved via a 0.062" grater screen. After subsequent blending, 4.38 kg glyceryl behenate were added and the mixture was blended to the press mixture.

The finished press mixture was transferred to a rotary tablet machine and compressed to oval biconvex tablets.

OPADRY® and purified water were added to a vessel under stirring. The mixture was stirred for at least 1 h. Then the suspension was passed through a sieve of a suitable size (e.g., 300 µm) and transferred into the solution tank of the coating pan (e.g., driacoater 1200). A film coating was applied on the cores under constant stirring of the suspension until the weight per coated tablet was 335 mg.

The tablets were subjected to stability testing at room temperature for 6 months in closed vials.

Table 9 shows the result of the stability testing of the composition produced by dry granulation compared to a composition produced by wet granulation according to Example 1.

TABLE 9

| Composition produced by | Hydrolyzation by weight | Total degradation by weight |
|---|---|---|
| Dry Granulation | 0.83 | 1.79 |
| Wet Granulation | 0.27 | 1.33 |

Hydrolyzation by weight refers to the percent by weight of Active Metabolite.

Total degradation by weight refers to the percent by weight of total degradation products of Fesoterodine.

7. In Vitro Dissolution Profile of Pharmaceutical Compositions Containing Various Amounts of HPMC The in-vitro dissolution profiles of Fesoterodine tablets with different HPMC contents were determined. The composition of the tablets is shown in Table 10 below.

TABLE 10

| | Formulation batch number | | | | | |
|---|---|---|---|---|---|---|
| | I | J | K | L | M | N |
| | Dosage | | | | | |
| | 4 mg [mg] | 4 mg [mg] | 4 mg [mg] | 8 mg [mg] | 8 mg [mg] | 8 mg [mg] |
| Fesoterodine/xylitol Granulate 1:9 | 40.00 | 40.00 | 40.00 | 80.00 | 80.00 | 80.00 |
| MICROCELAC ® 100 | 121.50 | 165.50 | 197.50 | 77.50 | 125.50 | 157.50 |
| METHOCEL ® K100M | 70.00 | 48.00 | 32.00 | 120.00 | 80.00 | 53.00 |
| METHOCEL ® K4M | 70.00 | 48.00 | 32.00 | 24.00 | 16.00 | 11.00 |
| Compritol 888 ATO | 10.00 | 10.00 | 10.00 | 10.00 | 10.00 | 10.00 |
| Talc | 8.50 | 8.50 | 8.50 | 8.50 | 8.50 | 8.50 |
| Total | 320.00 | 320.00 | 320.00 | 320.00 | 320.00 | 320.00 |

The in-vitro dissolution profiles were determined by the following analytical methods:

Drug release testing of Fesoterodine SR 4 mg and 8 mg tablets

| Dissolution parameters | |
|---|---|
| Dissolution Tester: | e.g. Erweka DT800 |
| Dissolution method: | according to USP <711> Drug Release, App. 2 |
| Temperature: | 37° C. ± 0.5° C. |
| RPM: | 75 |
| Sampling volume: | 5 mL (medium replacement after each sampling) |
| Sinker: | yes |
| Dissolution Medium: | phosphate buffer pH 6.8 |
| Chromatographic Conditions | |
| Column: | Spherisorb CN, 5 µm, 250 mm × 4 mm |
| Mobile phase: | Acetonitrile/Water/Trifluoro acetic acid 550:450:1 (v/v/v) |
| Flow rate: | 0.8 mL/min |
| Oven temperature: | 35° C. |
| Autosampler temperature: | 20° C. |
| Injection volume: | 50 µL |
| Detection: | UV at 220 nm |
| Retention times: | |
| Fesoterodine hydrogen fumarate | approx. 4.4 min |
| Active Metabolite | approx. 4.0 min |
| Run Time: | 6.5 min |

The dissolution results are shown in Table 11a (4 mg) and Table 11b (8 mg) below and in FIGS. 1A (4 mg) and 1B (8 mg).

TABLE 11a

| | Batch Number | | |
|---|---|---|---|
| | I | J | K |
| | Relative amount of HPMC | | |
| | 43.75 wt % | 30 wt % | 20 wt % |
| Time in hours | % Release of Fesoterodine hydrogen fumarate | | |
| 0 | 0 | 0 | 0 |
| 1 | 18 | 21 | 19 |
| 2 | 31 | 35 | 37 |
| 4 | 49 | 55 | 59 |
| 16 | 93 | 96 | 76 |

TABLE 11b

| | Batch Number | | |
|---|---|---|---|
| | L | M | N |
| | Relative amount of HPMC | | |
| | 45 wt % | 30 wt % | 20 wt % |
| Time in hours | % Release of Fesoterodine hydrogen fumarate | | |
| 0 | 0 | 0 | 0 |
| 1 | 18 | 21 | 23 |
| 2 | 31 | 37 | 40 |
| 4 | 50 | 60 | 63 |
| 16 | 93 | 100 | 96 |

Numbers refer to the percent release of Fesoterodine fumarate. The total amount of Fesoterodine fumarate in the tablets was 4 mg.

Based on these dissolution profiles the formulations having a HPMC content of over 30% (formulations "I" and "L") are particularly preferred. Another formulation matching the most preferred dissolution profile was formulation "O" given in Table 11c below:

TABLE 11c

| Formulation O Tablet Core | |
|---|---|
| Fesoterodine hydrogen fumarate | 4.0 |
| Xylitol | 76.0 |
| Lactose monohydrate | 43.0 |
| Microcrystalline cellulose | 41.5 |
| Hypromellose (e.g. METHOCEL ® K100M) | 70.0 |
| Hypromellose (e.g. METHOCEL ® K4M) | 70.0 |
| Glycerol dibehenate | 8.0 |
| Talc | 7.5 |
| Purified water | q.s.* |
| Film-coat | — |
| Total | 330.0 |

8. Lack of Electrocardiographic Effects of Fesoterodine Formulations

Fesoterodine formulations were administered orally to steady state at dosages of 4 mg and 28 mg per day to healthy male and female human subjects and the effect of such administration on QT values was determined.

The Fesoterodine 4 mg formulation was as follows. Higher dosage levels were obtained by administering multiple 4 mg formulations.

TABLE 12

| | |
|---|---|
| Fesoterodine fumarate | 4.0 |
| Xylitol | 36.0 |
| Lactose monohydrate | — |
| Microcryst. Cellulose | — |
| Lactose monohydrate (75%)/ microcryst. cellulose (25%) (e.g. Microcelac 100) | 121.5 |
| Hypromellose (e.g. Methocel K100M) | 70.0 |
| Hypromellose (e.g. Methocel K4M) | 70.0 |
| Glycerol dibehenate/glyceryl behenate | 10.0 |
| Talc | 8.5 |
| Purified water | q.s.[a] |
| Film-coat White | 10.0 |
| Purified water | q.s.[a] |
| Total | 330.0 |

[a] removed during drying of the wet granulate or during film-coating, to a residual moisture of approx. 2.5%
q.s. = quantum satis, as much as needed Steady state was determined by pharmacokinetic analysis of the Active Metabolite. Assay sensitivity was shown by a significant increase from baseline in QTcF and QTcI after multiple doses of moxifloxacin. The mean time-averaged QTcF increased by 8.6 ms after three days of treatment with moxifloxacin.

Multiple 4 mg and 28 mg doses of Fesoterodine did not exert an effect on myocardial repolarization, as shown by similar decreases from baseline in QTcF and QTcI between the Fesoterodine and placebo treated groups. The mean time-averaged QTcF decreased by 4.7 ms, 4.6 ms, and 5.0 ms after three days of treatment with placebo, 4 mg Fesoterodine, and 28 mg Fesoterodine, respectively. Outlier analyses revealed no differences between the Fesoterodine treatment groups and placebo. In contrast, a higher incidence of QTc outliers was seen after treatment with moxifloxacin.

The study design was double-blind, single-site, randomized, placebo- and positive controlled, parallel. Two hundred and fifty-six male and female subjects were assigned to one of the following four treatment groups (N=64 each; at least 50% female):

Fesoterodine 4 mg.day
Fesoterodine 28 mg/day
Moxifloxacin 400 mg/day
Placebo

Subjects were administered 3 days of one of the above four treatments. Three 12-lead ECGs were downloaded from an H-12 flash card (data carrier) at each of the following time points on Days −1, 1, and 3: 1, 2, 3, 4, 6, 8, 10, 12, 14, 16, 18, and 23.5 hours. Plasma samples for the determination of Active Metabolite concentration (and the concentration of further metabolites) were drawn on Day 1 and Day 3 predose and at 1, 2, 3, 4, 6, 8, 12, and 23.5 hours postdose.

Figure 2:
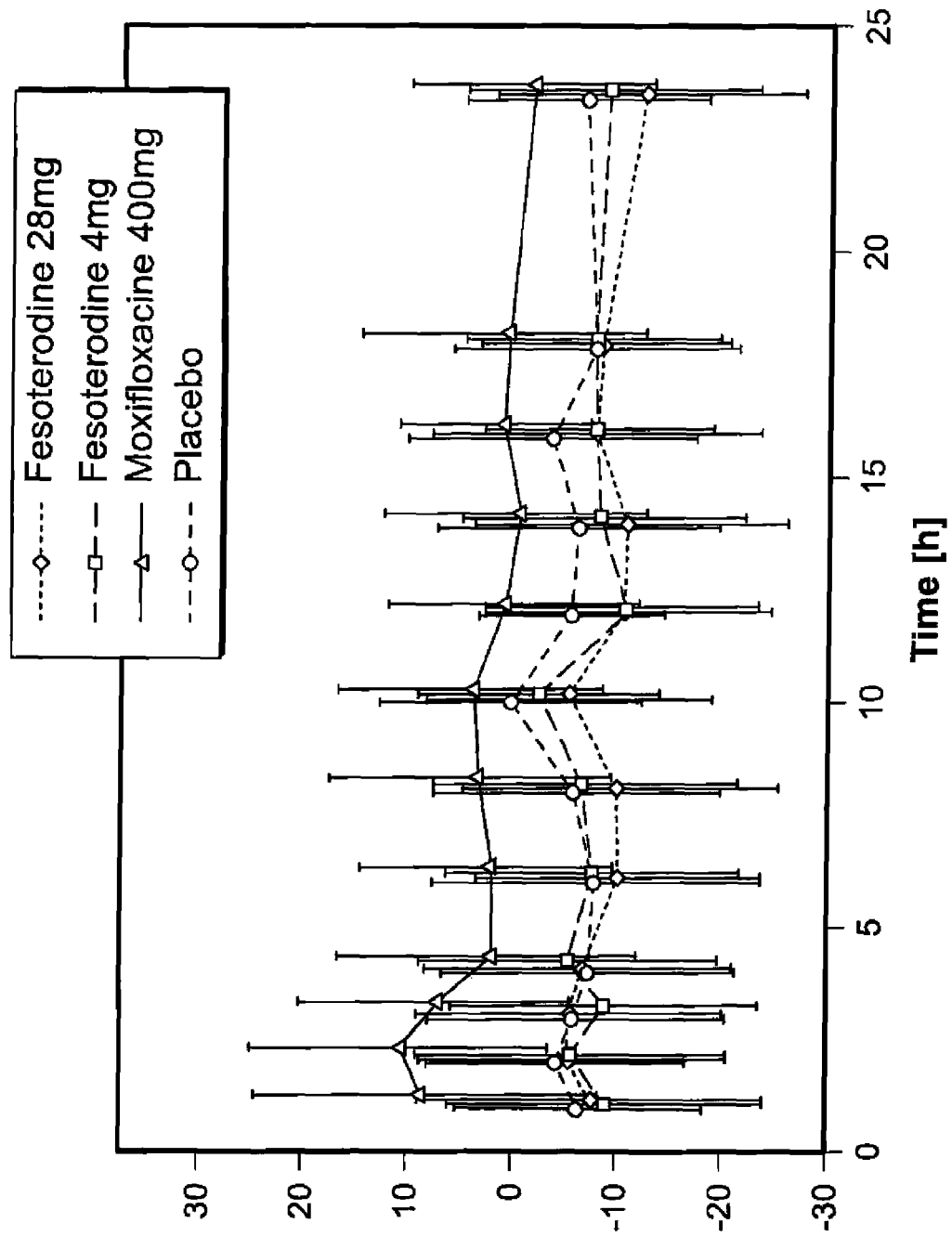
FIG. 2 shows the course of time-matched QTcF changes (±SD) from baseline after once-daily administrations of 4 mg or 28 mg Fesoterodine, 400 mg moxifloxacin, or placebo on day one.
Figure 3:
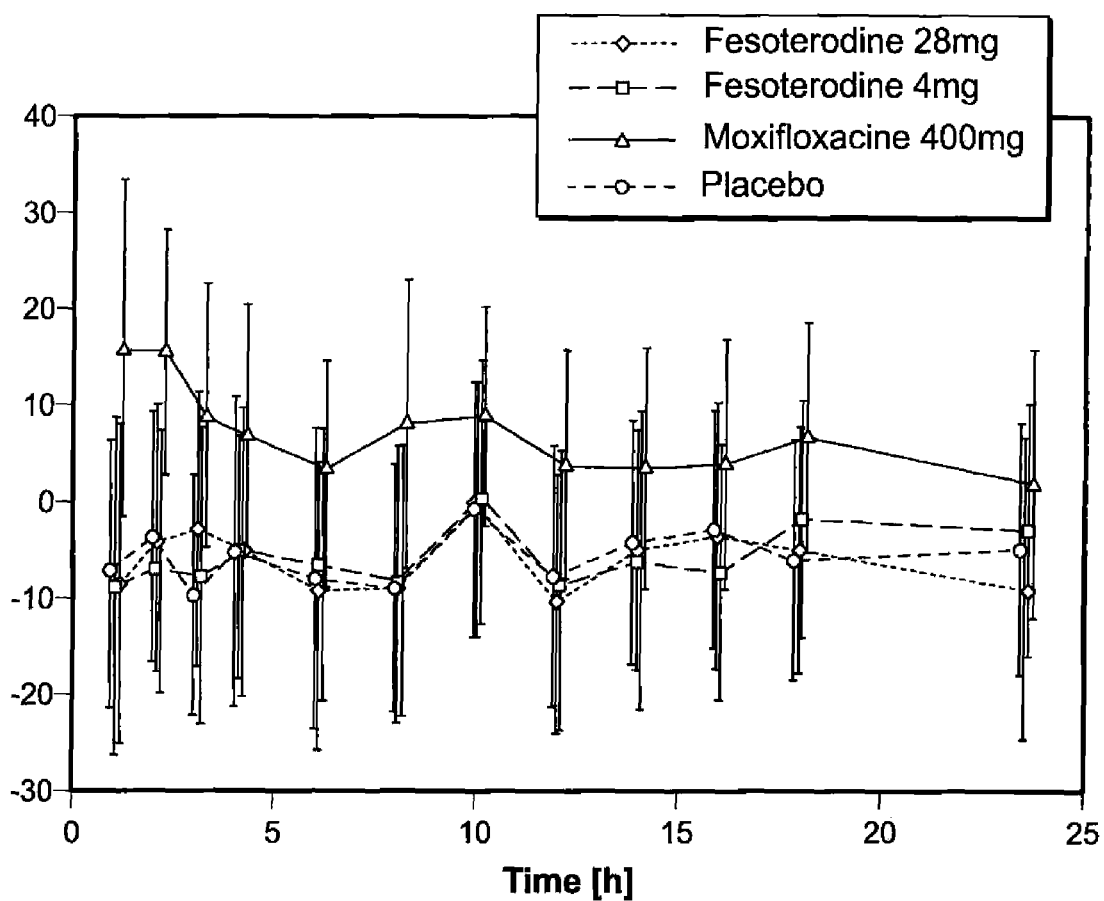
FIG. 3 shows the course of time-matched QTcF changes (±SD) from baseline after once-daily administrations of 4 mg or 28 mg Fesoterodine, 400 mg moxifloxacin, or placebo on day three.
Figure 4:
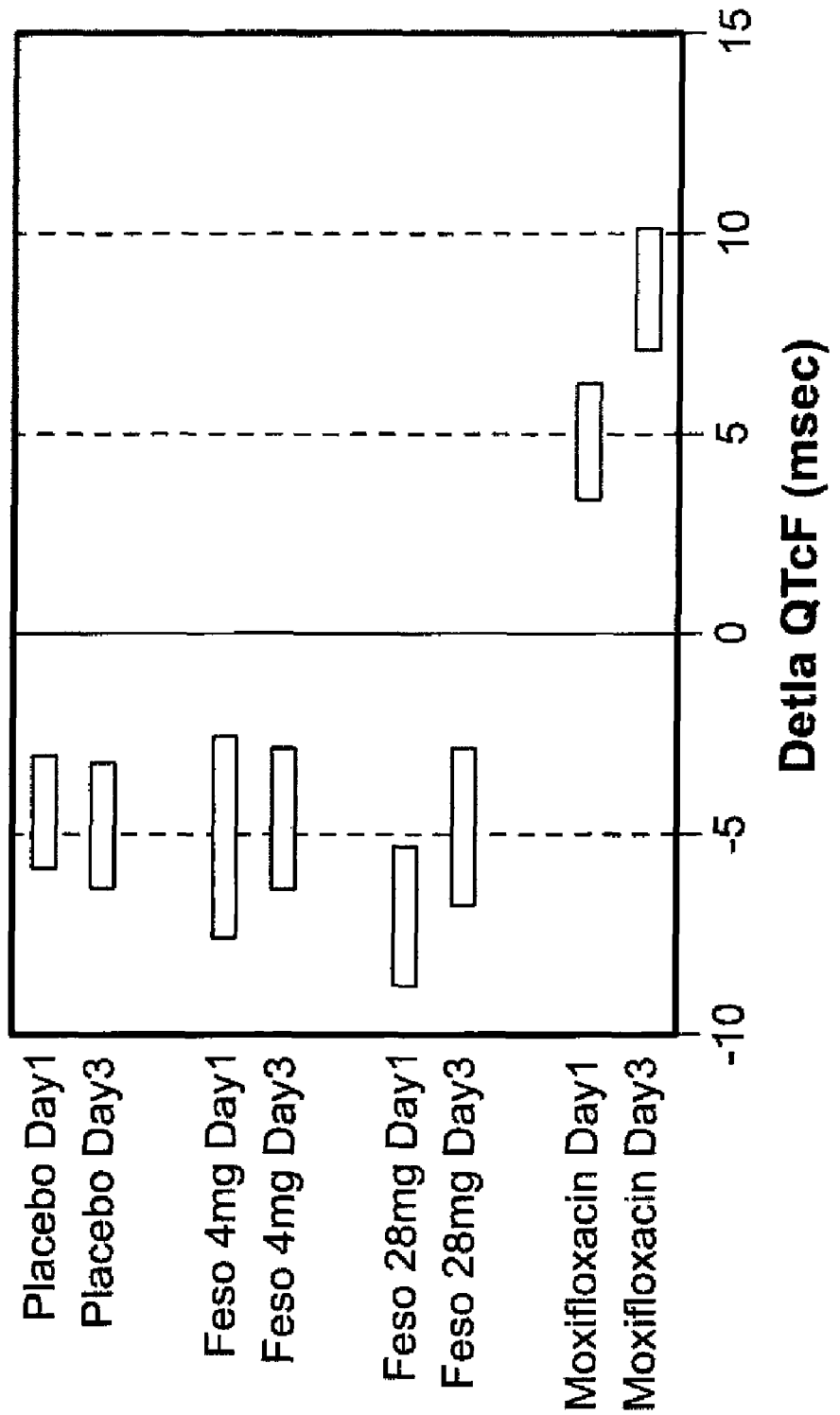
FIG. 4 shows the time-averaged changes (mean and 95% confidence interval) from baseline in QTcF after once-daily administrations of 4 mg or 28 mg Fesoterodine, 400 mg moxifloxacin, or placebo for three days.
Figure 5:
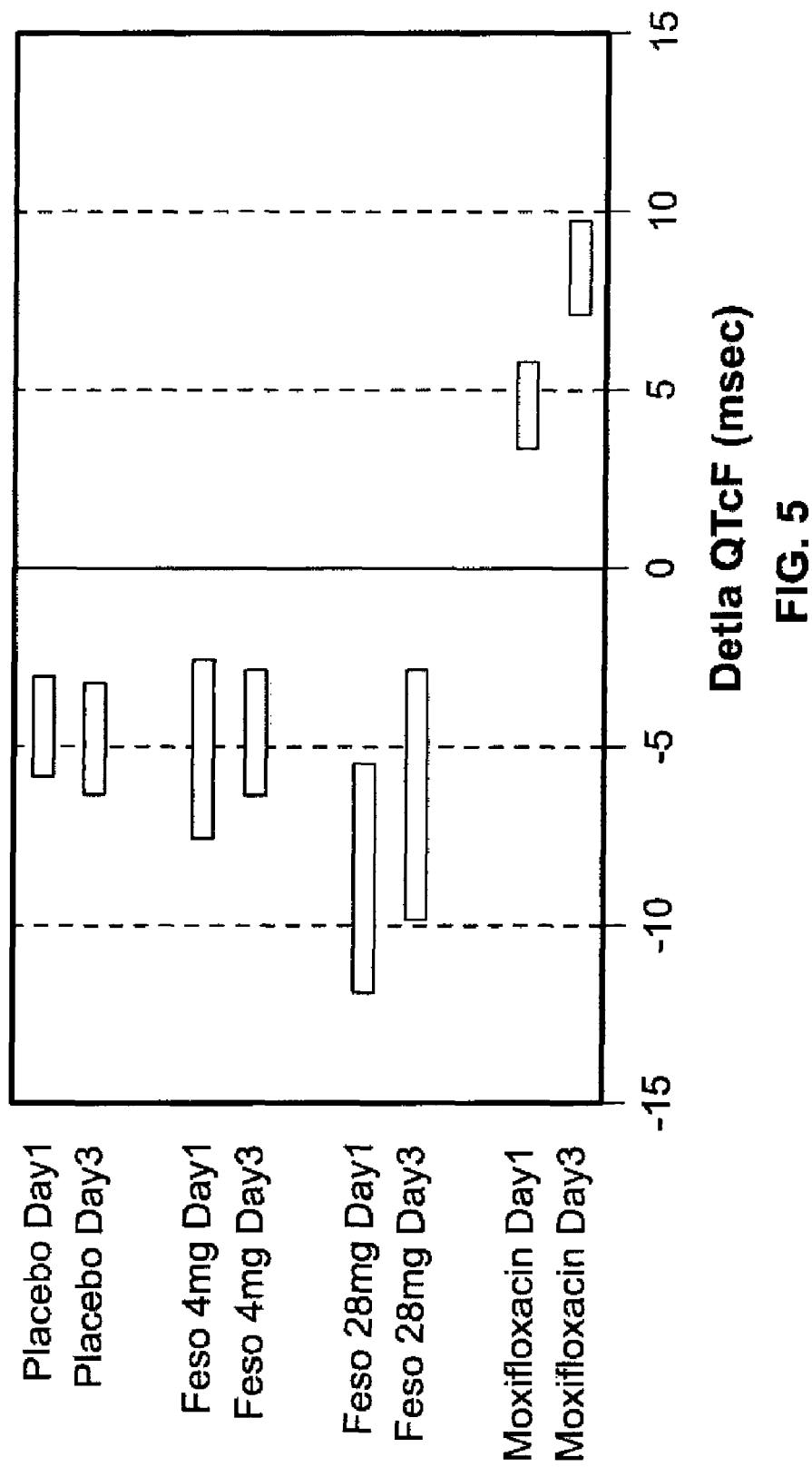
FIG. 5 shows the time-averaged changes (mean and 95% confidence interval) from baseline in QTcI after once-daily administrations of 4 mg or 28 mg Fesoterodine, 400 mg moxifloxacin, or placebo for three days.

FIG. 2 shows that results of the QTcF analyses on Day 1.
FIG. 3 shows that results of the QTcF analyses on Day 3.
FIG. 4 shows time-averaged changes in QTcF.
FIG. 5 shows time-averaged changes in QTcI.

Treatment with 4 mg or 28 mg Fesoterodine and with placebo resulted in a slight decrease of QTcF and QTcI with no significant difference between the active treatment groups and placebo. Assay sensitivity was shown by an increase of QTcF and QTcI after treatment with moxifloxacin, which was statistically significant as compared to Fesoterodine or placebo treatments. Outlier analysis revealed no differences between the Fesoterodine treatment groups and placebo, but a higher incidence after treatment with moxifloxacin was seen.

9. Comparison of the Efficacy of Fesoterodine Fumarate and Tolterodine Formulations A randomized, double-blind, double dummy, placebo and active-controlled trial in adult male and female human subjects was conducted. Once-daily 4 mg and 8 mg Fesoterodine fumarate was orally administered to patients with overactive bladder and compared to placebo and active-control (4 mg/day tolterodine 4 mg ER (extended release)).

The Fesoterodine formulations were as follows:

TABLE 13

| | 4 mg tablets | 8 mg tablets | 8 mg tablets |
|---|---|---|---|
| Fesoterodine fumarate | 4.0 | 8.0 | 8.0 |
| Xylitol | 36.0 | 72.0 | 72.0 |
| Lactose monohydrate | — | — | — |
| Microcryst. cellulose | — | — | — |
| Lactose monohydrate (75%)/ microcryst. cellulose (25%) (e.g. Microcelac 100) | 124.5 | 80.5 | 77.5 |
| Hypromellose (e.g. Methocel K100M) | 70.0 | 120.0 | 120.0 |
| Hypromellose (e.g. Methocel K4M) | 70.0 | 24.0 | 24.0 |
| Glycerol dibehenate/glyceryl behenate | 8.0 | 8.0 | 10.0 |
| Talc | 7.5 | 7.5 | 8.5 |
| Purified water | q.s.[a] | q.s.[a] | q.s.[a] |
| Film-coat White | 10.0 | 10.0 | 10.0 |
| Purified water | q.s.[a] | q.s.[a] | q.s.[a] |
| Total | 330.0 | 330.0 | 330.0 |

[a] removed during drying of the wet granulate or during film-coating, to a residual moisture of approx. 2.5%.
q.s. = quantum satis, as much as needed.
The two 8 mg formulations were used interchangeably.

The trial was conducted in 19 countries. A total of 1135 subjects were randomized and 1103 subjects were included in the full analysis set: 279 in the placebo treatment group, 265 in the 4 mg Fesoterodine treatment group, 276 in the 8 mg Fesoterodine treatment group, and 283 in the 4 mg tolterodine ER treatment group. The mean age of subjects was 57 years. A total of 81% were female and 97% were white. There were no notable differences among the treatment groups with respect to gender, race, age, or weight/BMI.

The efficacy results demonstrated statistically significant (all $p \leq 0.001$) improvements compared to placebo at the end of treatment in the primary variables requested by both the USFDA (change in average number of micturitions per 24 hours and change in the average number of urge incontinence episodes per 24 hours) and European regulatory authorities (change in average number of micturitions per 24 hours and treatment response (Yes/No variable) derived from a 4-category Treatment Benefit Scale). The decreases in the number of micturitions and urge incontinence episodes per 24 hours in the Fesoterodine 8 mg/day and 4 mg/day groups were significantly higher than in the placebo group. The treatment response rates also were higher at the end of treatment in both Fesoterodine dose groups compared to placebo. For all primary variables, Fesoterodine 4 mg/day demonstrated a slightly higher numerical change compared to placebo than tolterodine ER. This numerical difference was more pronounced for Fesoterodine 8 mg/day.

For the safety set, the number of patients were: 283 in the placebo treatment group, 272 in the Fesoterodine 4 mg/day treatment group, and 287 in the Fesoterodine 8 mg/day treatment group. The most common adverse events were typical of those observed in subjects taking marketed antimuscarinics.

Dry mouth occurred more frequently in Fesoterodine-treated subjects compared to placebo-treated subjects (Fesoterodine 4 mg/day 22%, Fesoterodine 8 mg/day 34%, placebo 7%). Constipation occurred more frequently in Fesoterodine-treated subjects compared to placebo-treated subjects (Fesoterodine 4 mg/day 3%, Fesoterodine 8 mg/day 5%, placebo 1%). Keratoconjunctivitis sicca occurred more frequently in Fesoterodine-treated subjects compared to placebo-treated subjects (Fesoterodine 4 mg/day 2%, Fesoterodine 8 mg/day 4%, placebo 0%). The incidence of dry throat was low in all groups ((Fesoterodine 4 mg/day 1%, Fesoterodine 8 mg/day 3%, placebo 0%) as was urinary retention (Fesoterodine 4 mg/day 1%, Fesoterodine 8 mg/day 1%, placebo 0%) and blurred vision (Fesoterodine 4 mg/day 1%, Fesoterodine 8 mg/day 1%, placebo 2%).

Table 14 shows the changes from baseline to end of treatment for the micturition and incontinence variables and the rates of treatment response.

TABLE 14

Changes from baseline for primary and co-primary variables at end of treatment[a] (FAS with LOCF)

| Variable | Pbo N = 279 Mean (SD) | Feso 4 mg/day N = 265 Mean (SD) | Feso 8 mg/day N = 276 Mean (SD) | Tolt 4 mg/day N = 283 Mean (SD) |
|---|---|---|---|---|
| Number of micturitions per 24 hours | −1.02 (2.97) | −1.74 (2.66) | −1.94 (3.15) | −1.69 (2.42) |
| Urge incontinence per 24 hours | −0.84 (2.94) | −1.44 (2.75) | −1.81 (2.35) | −1.43 (2.20) |
| Treatment response (responder rate) | 53% | 75% | 79% | 72% |

FAS = full analysis set,
feso = fesoterodine,
Tolt = tolterodine,
LOCF = last observation carried forward,
Pbo = placebo
[a]End of treatment is the last on-treatment visit based on an LOCF principle.
Data source: topline Table 13.1.1.1.1, Table 13.2.1.1.1, Table 13.3.1.1

Table 15 shows an ANCOVA analysis of the micturition variable.

TABLE 15

Ancova analysis of number of micturitions per 24 hours (FAS with LOCF)

| Variable | Treatment [n] | Endpoint LS Mean | Contrast | Treatment difference | ANCOVA p-value | 95% CI for the difference |
|---|---|---|---|---|---|---|
| Number of micturitions per 24 hours | Placebo [279] | −0.95 | | | | |
| | Feso 4 mg [265] | −1.76 | 4 mg vs Pbo | −0.81 | <0.001 | (−1.26, −0.36) |
| | Feso 8 mg [276] | −1.88 | 8 mg vs Pbo | −0.93 | <0.001 | (−1.38, −0.49) |
| | Tolt 4 mg [283] | −1.73 | Tolt 4 mg vs Pbo | −0.78 | 0.001 | (−1.23, −0.34) |

FAS = full analysis set,
feso = fesoterodine,
tolt = tolterodine,
LOCF = last observation carried forward,
Pbo = placebo,
CI = confidence interval
Data source: topline Table 13.1.2.1.1

Table 16 shows an ANCOVA analysis of the urge incontinence variable.

TABLE 16

Ancova analysis of urge incontinence per 24 hours
(FAS with LOCF)

| Variable | Treatment [n] | Endpoint LS Mean | Contrast | Treatment difference | ANCOVA p-value | 95% CI for the difference |
|---|---|---|---|---|---|---|
| Urge incontinence per 24 hours | Placebo [211] | −1.14 | | | | |
| | Feso 4 mg [199] | −1.95 | 4 mg vs Pbo | −0.81 | 0.001 | (−1.26, −0.35) |
| | Feso 8 mg [223] | −2.22 | 8 mg vs Pbo | −1.08 | <0.001 | (−1.52, −0.64) |
| | Tolt 4 mg [223] | −1.74 | Tolt 4 mg vs Pbo | −0.60 | 0.008 | (−1.04, −0.16) |

FAS = full analysis set,
feso = fesoterodine,
tolt = tolterodine,
LOCF = last observation carried forward,
Pbo = placebo,
CI = confidence interval
Data source: topline Table 13.2.2.1.1
The decreases in the number of micturitions and number of urge incontinence episodes per 24 hours in the Fesoterodine 8

The decreases in the number of micturitions and number of urge incontinence episodes per 24 hours in the Fesoterodine 8 mg/day and 4 mg/day groups were significantly higher than in the placebo group. The treatment response rates were also higher at the end of treatment in both Fesoterodine dose groups compared to placebo.

Figure 6:
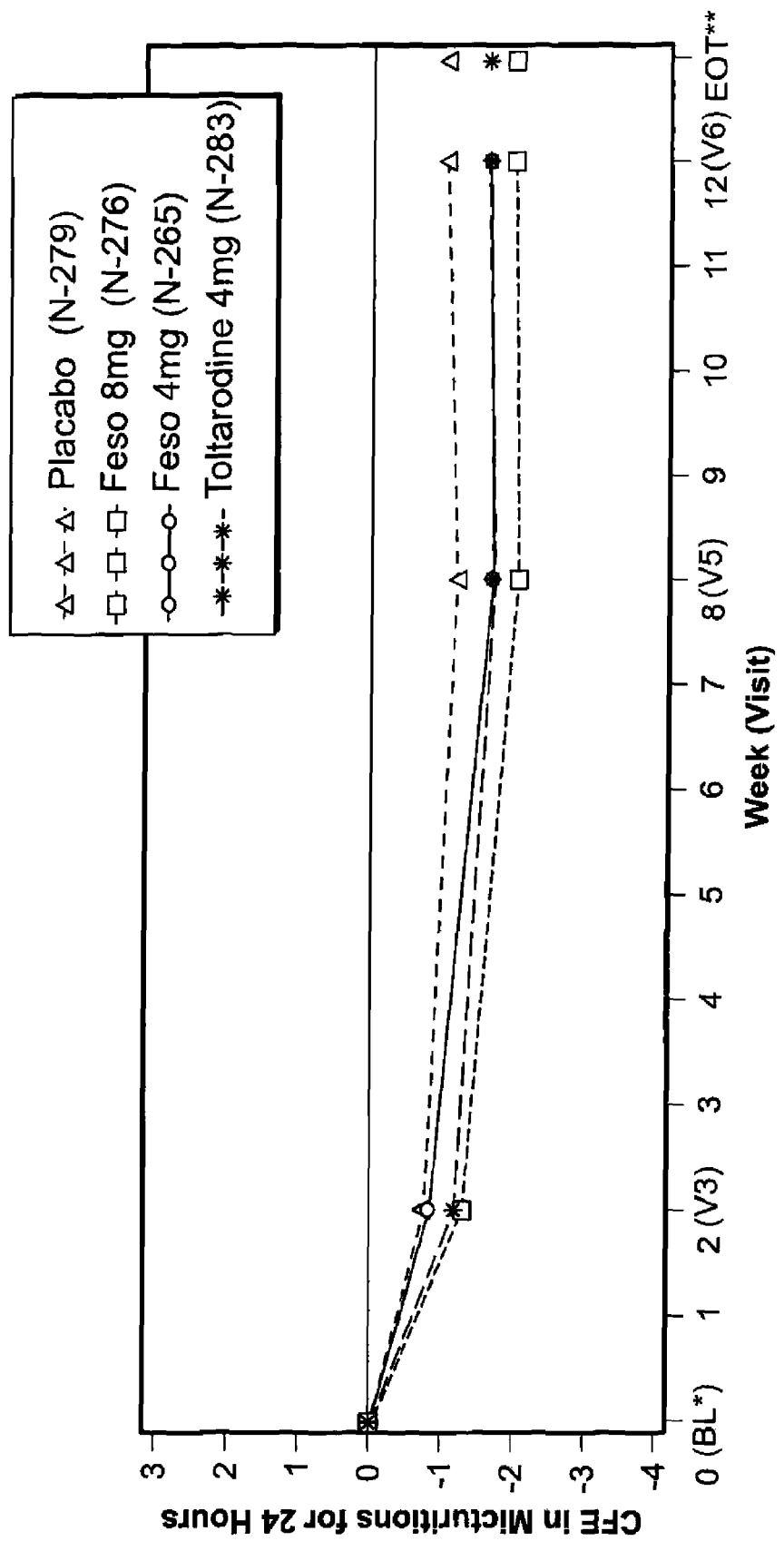
FIG. 6 shows the change from baseline in average frequency of micturitions per 24 hours for the trial comparing Fesoterodine 4 mg/day, Fesoterodine 8 mg/day, tolterodine 4 mg/day, and placebo.
Figure 7:
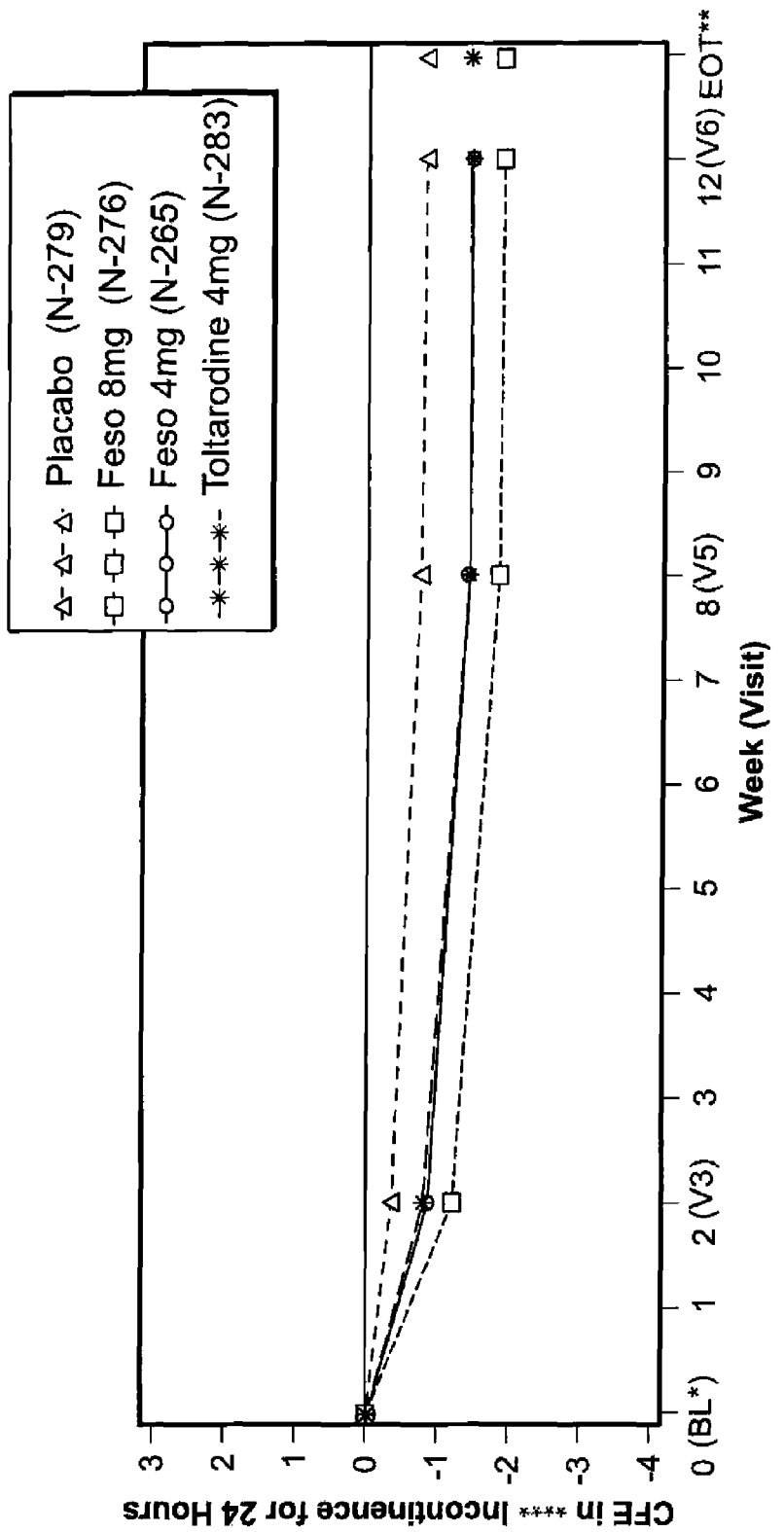
FIG. 7 shows the change from baseline in average number of incontinence episodes per 24 hours for the trial comparing Fesoterodine 4 mg/day, Fesoterodine 8 mg/day, tolterodine 4 mg/day, and placebo.
Figure 8:
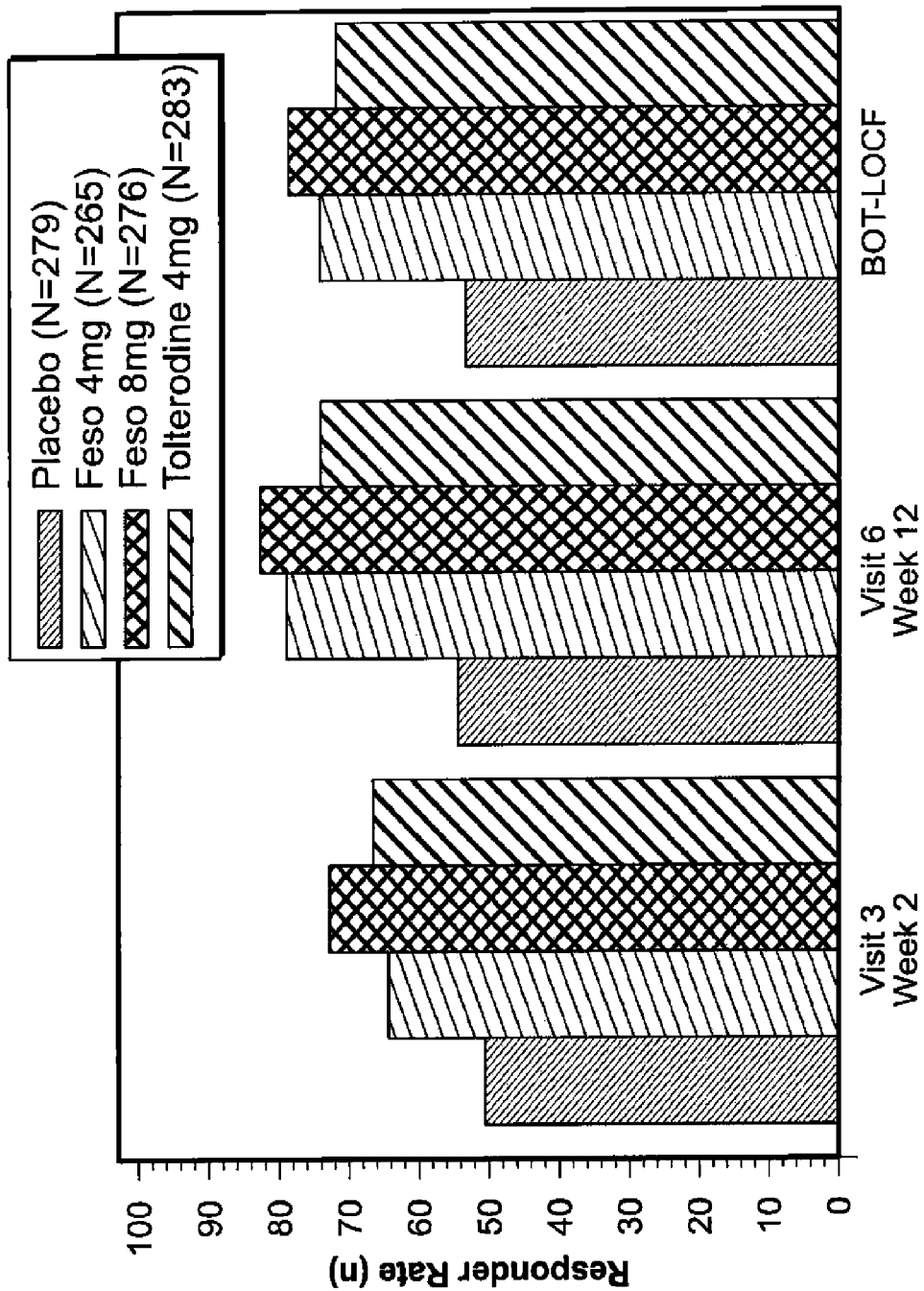
FIG. 8 shows the treatment benefit scale for the trial comparing Fesoterodine 4 mg/day, Fesoterodine 8 mg/day, tolterodine 4 mg/day, and placebo.

FIGS. 6, 7, and 8 illustrate the changes from baseline by treatment visit for the three primary variables. Improvements in all three primary variables were observed as early as after two weeks of treatment (Visit 3=first point of post-baseline measurement).

A summary of the results of the closed testing procedure is provided in Table 17.

TABLE 17

Summary of statistical analyses of primary efficacy
variables using closed testing procedures (FAS with LOCF)

| Testing procedure | p-value[a] | Significant[b] |
|---|---|---|
| United States Food and Drug Administration | | |
| Step 1: Number of micturitions per 24 hours Feso 8 mg/day vs pbo | <0.001 | Yes |
| Step 2: Number of micturitions per 24 hours Feso 4 mg/day vs pbo | <0.001 | Yes |
| Step 3: Number of urge incontinence episodes per 24 hours Feso 8 mg/day vs pbo | <0.001 | Yes |
| Step 4: Number of urge incontinence episodes per 24 hours Feso 4 mg/day vs pbo | 0.001 | Yes |
| European Regulatory Authorities | p-value[a] | Significant[c] |
| Step 1: Feso 8 mg/day vs pbo | | Yes |
| a) Number of micturitions per 24 hours | <0.001 | |
| b) Treatment response | <0.001 | |

TABLE 17-continued

Summary of statistical analyses of primary efficacy
variables using closed testing procedures (FAS with LOCF)

| Step 2: Feso 4 mg/day vs pbo | | Yes |
|---|---|---|
| a) Number of micturitions per 24 hours | <0.001 | |
| b) Treatment response | <0.001 | |

FAS = full analysis set, LOCF = last observation carried forward

[a]Number of micturitions and urge incontinence episodes analysed with an ANCOVA model with terms for treatment and region and baseline value as a covariate. Treatment response is analyzed using a normal approximation method for binary data.
[b]Significant based on closed testing procedure. Each step tested at 0.05 two-sided (0.025 one-sided). If result was not significant at any step, then all steps after that are considered not statistically significant.
[c]Significant based on closed testing procedure. If both p-values at Step 1 are less than 0.05 two-sided (0.025 one-sided), then 8 mg results are statistically significant. If Step 1 is statistically significant and both p-values at Step 2 are less than 0.05 two-sided (0.025 one-sided), then 4 mg results are statistically significant.

NOTE:
All results are at the end of treatment using LOCF for missing values

For the USFDA analysis, all 4 p-values in the closed testing procedure were less than 0.05. Therefore, both Fesoterodine doses (4 mg and 8 mg/day) showed statistically significant improvement over placebo at end of treatment for the micturitions and urge incontinence variables.

Similarly, for the European regulatory authorities analysis, all 4 p-values in the closed testing procedure were less than 0.05. Therefore, both Fesoterodine doses (4 mg and 8 mg/day) showed statistically significant improvement over placebo at end of treatment for the micturitions and treatment response variables.

Treatment-emergent adverse events were reported for 107/283 (38%) of subject in the placebo group, 135/272 (50%) of subjects in the Fesoterodine 4 mg/day group, and 167/287 (58%) of subjects in the Fesoterodine 8 mg/day group.

Table 18 summarizes the most common adverse events during the overall treatment period (i.e., adverse events with an incidence of ≧3% in a treatment group) and other relevant adverse events ≦3%,

TABLE 18

Summary of subject with treatment-emergent adverse events reported by ≧3% of subjects in at least one treatment group

| MedDRA system organ class/preferred term | Pbo N = 283 n (%) | Feso 4 mg/day N = 272 n (%) | Feso 8 mg/day N = 287 n (%) |
|---|---|---|---|
| Any adverse event | 107 (38) | 135 (50) | 167 (58) |
| Eye disorders | | | |
| Keratoconjunctivitis sicca | 0 | 6 (2) | 12 (4) |
| Gastrointestinal disorders | | | |
| Mouth dry | 20 (7) | 59 (22) | 97 (34) |
| Constipation | 4 (1) | 9 (3) | 13 (5) |
| General disorders and administration site conditions | | | |
| Fatigue | 1 (<1) | 1 (<1) | 1 (<1) |
| Infections and infestations | | | |
| Urinary tract infection | 6 (2) | 8 (3) | 9 (3) |
| Nasopharyngitis | 7 (3) | 8 (3) | 5 (2) |
| Influenza | 6 (2) | 9 (3) | 2 (<1) |
| Nervous system disorders | | | |
| Headache | 14 (5) | 12 (4) | 7 (2) |

SS = safety set

10. Pharmacokinetics of Fesoterodine fumarate formulations

A randomized, double-blind, placebo-controlled trial in adult, healthy male human subjects was conducted in which the pharmacokinetics of Fesoterodine fumarate formulations at 4 mg, 8 mg, 12, mg, 20 mg, and 28 mg once-daily for three days was determined.

Fesoterodine 4 mg formulation used was as follows. Higher dosage levels were obtained by administering multiple 4 mg formulations.

TABLE 19

| | |
|---|---|
| Fesoterodine fumarate | 4.0 |
| Xylitol | 76.0 |
| Lactose monohydrate | 43.0 |
| Microcryst. cellulose | 41.5 |
| Lactose monohydrate (75%)/ microcryst. cellulose (25%) (e.g. Microcelac 100) | — |
| Hypromellose (e.g. Methocel K100M) | 70.0 |
| Hypromellose (e.g. Methocel K4M) | 70.0 |
| Glycerol dibehenate/glyceryl behenate | 8.0 |
| Talc | 7.5 |
| Purified water | q.s.[a] |
| Film-coat | — |
| Purified water | q.s.[a] |
| Total | 320.0 |

[a] removed during drying of the wet granulate or during film-coating, to a residual moisture of approx. 2.5%
q.s. = quantum satis, as much as needed 40 subjects were randomized. The subjects were healthy Caucasian males, aged from 18 to 50 years, with a normal body weight as determined by body mass index ranging between 20 to 28 $kg/m^2$ and having normal laboratory findings with respect to blood pressure, heart rate, and ECG.

Non-compartmental pharmacokinetic parameters were derived from the individual concentration time curves of Active Metabolite of Fesoterodine based on scheduled blood sampling times as well as from the individual amounts of Active Metabolite excreted into urine and based on actual urine collection.

All statistical summaries and displays were done based on scheduled sampling times unless there were significant deviations of actual sampling times from scheduled sampling times.

Plasma concentrations of Active Metabolite were displayed as individual plasma concentration-time curves after single dose as measured and after log-transformation. Summaries and displays of plasma concentrations of Active Metabolite were done according to the following specifications:

Mean concentration-time curves (means ±SD) were generated according to the following rules: Mean concentrations were only calculated if at least 2/3 (this was 4 in this trial) of the concentrations were above LOQ. This was done to avoid that means towards the end of the measurement period were biased by only few values above LOQ. All values below LOQ were discarded. Descriptive statistics including geometric means and geometric SD, were calculated and tabulated per scheduled sampling time.

For the calculation of individual pharmacokinetic profile parameters, concentration values were handled as specified above. Parameters were listed for all subjects and summarized by dose level and period by means of descriptive statistics, including geometric mean, geometric SD including 90% confidence intervals for the geometric means. These confidence intervals were derived via exponential retransformation of the corresponding confidence intervals for means of the log-transformed data. For $t_{max}$, a frequency table was also provided.

For the assessment of dose linearity of Active Metabolite, $C_{max}$, and AUC were dose normalized. The resulting dose-adjusted parameters were then subjected to a one-way ANOVA with dose as "treatment" factor. The dose-adjusted parameters were log-transformed prior to submission to the ANOVA. Dose dependency of these pharmacokinetic parameters (without dose adjustment) were also assessed graphically.

An evaluation of the amounts of Active Metabolite excreted into urine was done similarly to the procedures outlined above for the plasma concentrations. Cumulative excretion time curves were generated. The total amount excreted into urine and the amount excreted into urine on Day 3 were subjected to the same statistical procedures as outlined for the plasma concentrations.

Table 20 shows the pharmacokinetic results.

TABLE 20

| Day | Parameter | 4 mg Mean(SD) | 8 mg Mean(SD) | 12 mg Mean(SD) | 20 mg Mean(SD) | 28 mg Mean(SD) |
|---|---|---|---|---|---|---|
| 1 | Cmax (ng/mL) | 2.19(0.66) | 4.31(1.79) | 5.88(3.21) | 12.36(6.07) | 16.29(5.69) |
| | tmax (hr) | 5.17(0.75) | 4.83(0.75) | 5.00(0.00) | 5.50(0.55) | 5.60(0.66) |
| | Ctrough (ng/mL) | 0.01(0.02) | 0.00(0.00) | 0.00(0.00) | 0.00(0.00) | 0.00(0.00) |

TABLE 20-continued

| Day | Parameter | 4 mg Mean(SD) | 8 mg Mean(SD) | 12 mg Mean(SD) | 20 mg Mean(SD) | 28 mg Mean(SD) |
|---|---|---|---|---|---|---|
| | Lambdaz (1/hr) | 0.12(0.03) | 0.10(0.02) | 0.11(0.03) | 0.12(0.02) | 0.11(0.04) |
| | t½ (hr) | 6.11(1.15) | 7.42(2.03) | 6.75(2.57) | 5.87(0.79) | 6.94(3.13) |
| | AUC0-24 (hr * ng/mL) | 17.99(7.16) | 44.48(17.47) | 61.81(18.43) | 126(49) | 181(59.74) |
| | AUC0-inf (hr * ng/mL) | 20.09(8.60) | 51.79(20.66) | 69.29(18.20) | 137(54.28) | 208(68.96) |
| | Ae (mcg) | 263(88.2) | 662(246) | 1132(479) | 1678(506) | 1681(640) |
| 2 | Cmax (ng/mL) | 1.92(0.84) | 3.73(1.35) | 5.63(1.59) | 12.01(5.86) | 18.14(3.57) |
| | tmax (hr) | 5.67(0.82) | 5.67(0.82) | 5.67(0.82) | 5.67(0.82) | 6.00(0.00) |
| | Ctrough (ng/mL) | 0.22(0.14) | 0.62(0.33) | 0.73(0.22) | 1.31(0.65) | 2.26(1.46) |
| | AUC0-24 (hr * ng/mL) | 21.39(9.60) | 44.62(17.00) | 63.97(16.11) | 126(60.42) | 204(50.74) |
| | Ae (mcg) | 305(127) | 708(305) | 1178(515) | 1744(420) | 2542(646) |
| 3 | Cmax (ng/mL) | 2.12(1.28) | 5.15(2.02) | 7.11(3.01) | 13.25(7.25) | 18.28(6.31) |
| | tmax (hr) | 4.17(2.04) | 5.00(0.00) | 5.67(1.21) | 5.33(0.52) | 5.17(0.41) |
| | Ctrough (ng/mL) | 0.37(0.19) | 0.74(0.33) | 0.82(0.37) | 1.41(0.72) | 2.81(1.61) |
| | Lambdaz (1/hr) | 0.12(0.07) | 0.11(0.02) | 0.11(0.03) | 0.12(0.03) | 0.09(0.04) |
| | t½ (hr) | 7.76(4.09) | 6.54(0.91) | 6.37(1.55) | 6.07(1.16) | 8.04(2.07) |
| | AUC0-24 (hr * ng/mL) | 20.26(11.44) | 52.03(21.76) | 72.87(25.37) | 136(68.78) | 213(73.28) |
| | CLtot/f (L/min) | 5.81(6.63) | 3.41(2.83) | 3.10(1.29) | 2.89(1.10) | 2.42(0.80) |
| | MRT (hr) | 12.97(5.65) | 10.79(0.87) | 11.26(1.94) | 10.99(1.68) | 13.39(2.69) |
| | Vz/f (L) | 2749(1447) | 1639(1154) | 1756(947) | 1551(624) | 1683(717) |
| | Ae (mcg) | 317(184) | 671(307) | 1364(487) | 1757(363) | 2426(593) |
| | Clren (L/min) | 0.26(0.07) | 0.21(0.04) | 0.33(0.10) | 0.24(0.06) | 0.20(0.07) |

What is claimed is:

1. A pharmaceutical composition comprising:
   (a) 0.3-5.0% [w/w] of fesoterodine hydrogen fumarate;
   (b) 5-25% [w/w] sorbitol or xylitol;
   (c) 20-40% [w/w] of a mixture comprising 45-80% (w/w) lactose monohydrate and 55-20% (w/w) microcrystalline cellulose;
   (d) 20-65% hydroxypropyl methylcellulose;
   (e) 1-5% [w/w] glycerol dibehenate; and
   (f) 1-5% [w/w] talc.

2. The pharmaceutical composition of claim 1, comprising:
   (a) about 4.0 mg fesoterodine hydrogen fumarate
   (b) about 32-40 mg of xylitol with a mean particle size of about 0.001-0.30 mm
   (c) about 115-130 mg of a mixture of lactose monohydrate and microcrystalline cellulose
   (d) about 65-75 mg of HPMC (Hydroxypropyl methylcellulose) having a nominal viscosity of about 100,000 mPa·s when dissolved (about 2% by weight) in water
   (e) about 65-75 mg of HPMC (Hydroxypropyl methylcellulose) having a nominal viscosity of about 4,000 mPa·s when dissolved about 2% by weight) in water
   (f) about 8-12 mg of glycerol dibehenate
   (g) about 7-10 mg talc, and, optionally,
   (h) a coating.

3. The pharmaceutical composition of claim 1, comprising:
   (a) about 8.0 mg fesoterodine hydrogen fumarate
   (b) about 65-80 mg of xylitol with a mean particle size of about 0.001-0.30 mm
   (c) about 70-85 mg of a mixture of lactose monohydrate and microcrystalline cellulose
   (d) about 110-130 mg of HPMC (Hydroxypropyl methylcellulose) having a nominal viscosity of about 100,000 mPa·s when dissolved (about 2% by weight) in water
   (e) about 20-30 mg of HPMC (Hydroxypropyl methylcellulose) having a nominal viscosity of about 4,000 mPa·s when dissolved about 2% by weight) in water
   (f) about 8-12 mg of glycerol dibehenate
   (g) about 7-10 mg talc, and, optionally,
   (h) a coating.

4. A method of treating a patient suffering from overactive bladder by administering a therapeutically effective amount of a pharmaceutical composition according to claim 1 to said patient.

5. The method according to claim 4, wherein the patient has symptoms selected from the group consisting of urinary incontinence, urinary urge incontinence, imperative urinary urge, and/or increased urinary frequency.

6. A method for preparing a pharmaceutical composition according to claim 1, comprising mixing fesoterodine or a pharmaceutically acceptable salt thereof with a stabilizer selected from the group consisting of xylitol or sorbitol, and combinations thereof.

7. The method according to claim 6, which further comprises a granulation step.

8. The method according to claim 7, wherein the granulation is wet granulation.

9. The method according to any one of claims 6-8, comprising
   granulating fesoterodine or a pharmaceutically acceptable salt thereof with a stabilizer selected from the group consisting of xylitol or sorbitol and combinations thereof in the presence of water,
   drying the granulate,
   mixing the dried granulates with at least one other excipient to give a compression mixture,
   compressing the compression mixture to the desired form, and
   optionally applying a coating.

* * * * *